US006991874B1

(12) United States Patent
Möhwald et al.

(10) Patent No.: US 6,991,874 B1
(45) Date of Patent: *Jan. 31, 2006

(54) COMPOSITIONS SUITABLE FOR ELECTROCHEMICAL CELLS

(75) Inventors: Helmut Möhwald, Annweiler (DE); Gerhard Dötter, Ludwigshafen (DE); Rainer Blum, Ludwigshafen (DE); Peter Keller, Spiesen-Elversberg (DE); Stephan Bauer, Hochdorf-Assenheim (DE); Bernd Bronstert, Otterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/674,541

(22) PCT Filed: May 4, 1999

(86) PCT No.: PCT/EP99/03028

§ 371 (c)(1),
(2), (4) Date: Nov. 2, 2000

(87) PCT Pub. No.: WO99/57161

PCT Pub. Date: Nov. 11, 1999

(30) Foreign Application Priority Data

May 4, 1998 (DE) ............................. 198 19 752

(51) Int. Cl.
*H01M 2/14* (2006.01)

(52) U.S. Cl. ............... 429/129; 429/217; 429/218.1; 429/231.1; 429/231.8; 429/231.95; 429/229; 429/144; 429/309; 429/247; 429/249; 429/231.5; 429/231; 252/62.2; 521/27; 428/411.1; 428/473.5; 428/474.4

(58) Field of Classification Search ................ 429/217, 429/218.1, 231.1, 231.8, 231.95, 229, 144, 429/129, 309, 247, 249, 231, 231.5; 428/411.1, 428/473.5, 474.4; 521/27; 252/62.2
See application file for complete search history.

(56) References Cited

U.S. PATENT DOCUMENTS

| 4,241,149 A | 12/1980 | Labes et al. ............ 429/50 |
| 5,073,611 A | 12/1991 | Rehmer et al. ......... 526/208 |
| 5,098,973 A | 3/1992 | Kozuka et al. .......... 526/282 |
| 5,128,386 A | 7/1992 | Rehmer et al. ........... 522/35 |
| 5,296,318 A | 3/1994 | Gozdz et al. ........... 429/192 |
| 5,420,204 A | 5/1995 | Valet et al. ............. 525/125 |
| 5,429,891 A | 7/1995 | Gozdz et al. ........... 429/192 |
| 5,486,435 A | 1/1996 | Brochu et al. .......... 429/192 |
| 5,558,911 A | 9/1996 | Blum .................... 429/517 |
| 5,622,792 A | 4/1997 | Brochu et al. .......... 429/192 |
| 5,643,695 A * | 7/1997 | Barker et al. ........... 429/217 |
| 6,475,663 B1 * | 11/2002 | Mohwald et al. ........ 429/129 |
| 6,632,561 B1 * | 10/2003 | Bauer et al. ............ 429/144 |

FOREIGN PATENT DOCUMENTS

| DE | 44 33 290 | 3/1996 |
| DE | 196 12 769 | 10/1997 |
| DE | 196 53 631 | 6/1998 |
| WO | WO 99/19917 | * 4/1999 |

OTHER PUBLICATIONS

G. Eisele et al. "Mécanisme do photoréticulation de polymères contenant le motif dicyclopentadiène en présence et absence de benzophénone" Macromolecular Chem. vol. 197, (1996) pp. 1731-1756.

Ullmann's Encyclopedia of Industrial Chemistry 5th Ed., vol. A3 pp. 343-397.

* cited by examiner

*Primary Examiner*—Laura Weiner
(74) *Attorney, Agent, or Firm*—Novak Druce & Quigg, LLP

(57) ABSTRACT

The compositions comprise:
(a) from 1 to 99% by weight of a pigment (I) having a primary particle size of from 5 nm to 100 μm which is a solid Ia or a compound Ib which acts as cathode material in electrochemical cells or a compound Ic which acts as anode material in electrochemical cells or a mixture of the solid Ia with the compound Ib or the compound Ic,
(b) from 1 to 99% by weight of a polymeric material (II) which comprises:
(IIa) from 1 to 100% by weight of a polymer or copolymer (IIa) which has, as part of the chain, at the end(s) of the chain and/or laterally on the chain, reactive groups (RG) which are capable of crosslinking reactions under the action of heat and/or UV radiation, and
(IIb) from 0 to 99% by weight of at least one polymer or copolymer (IIb) which is free of reactive groups RG.

10 Claims, 3 Drawing Sheets

COMPOSITIONS SUITABLE FOR ELECTROCHEMICAL CELLS

Figure 1:
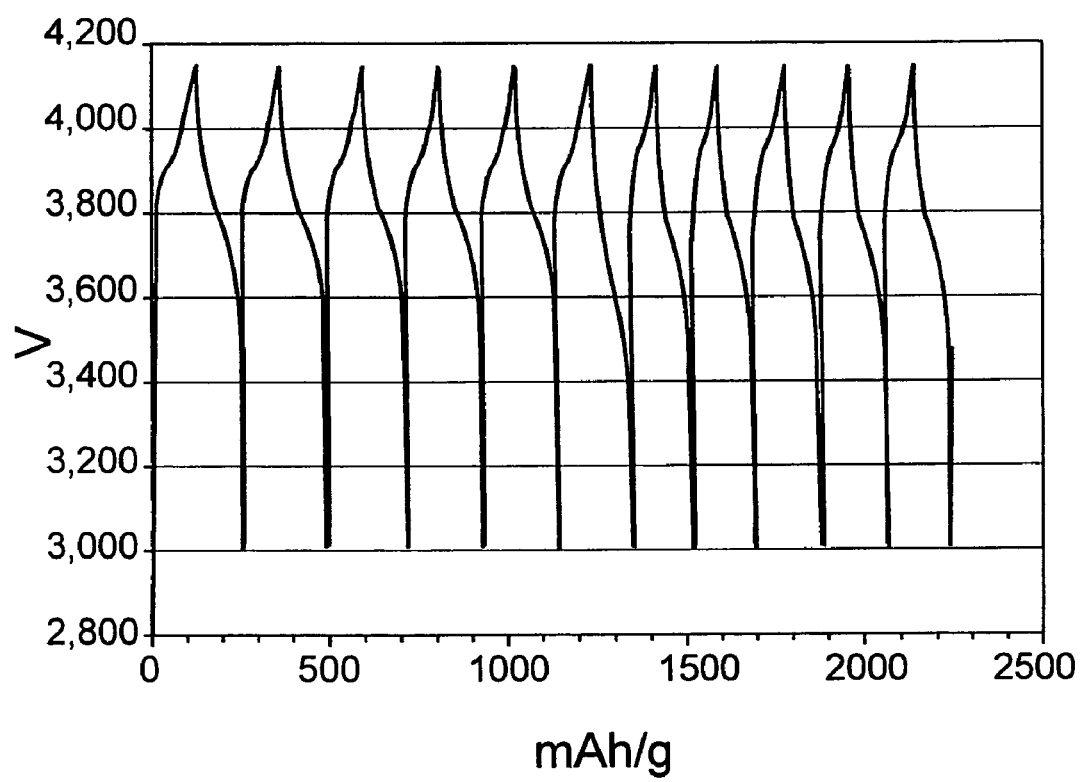

The present invention relates to compositions which are suitable, inter alia, for electrochemical cells having lithium ion-containing electrolytes, to their use, for example, in or as solid electrolytes, separators and electrodes, to solid electrolytes, separators, electrodes, sensors, electrochromic windows, displays, capacitors and ion-conducting films in which such a composition is present and to electrochemical cells comprising such solid electrolytes, separators and/or electrodes.

Electrochemical, in particular rechargeable, cells are generally known, for example from "Ullmann's Encyclopedia of Industrial Chemistry", 5th edition, vol A3, VCH Verlagsgesellschaft mbH, Weinheim, 1985, pages 343–397.

Among these cells, lithium batteries and lithium ion batteries occupy a special position, particularly as secondary cells, because of their high specific energy storage density.

The cathode of such cells comprises, as described, for example, in the above citation from "Ullmann", lithiated mixed oxides of manganese, cobalt, vanadium or nickel, as can be described in the stoichio-metrically simplest case as $LiMn_2O_4$, $LiCoO_2$, $LiV_2O_5$ or $LiNiO_2$.

These mixed oxides react reversibly with compounds which can incorporate lithium ions into their lattice, e.g. graphite, to release the lithium ions from the crystal lattice, with the metal ions such as manganese, cobalt or nickel ions being oxidized in the latter. This reaction can be used for the storage of electric power in an electrochemical cell by separating the compound which takes up lithium ions, i.e. the anode material, and the lithium-containing mixed oxide, i.e. the cathode material by an electrolyte through which the lithium ions migrate from the mixed oxide into the anode material (charging process).

The compounds which are suitable for the reversible storage of lithium ions are customarily fixed to contact electrodes by means of a binder.

During charging of the cell, electrons flow through an external power source and lithium cations flow through the electrolyte to the anode material. When the cell is used, the lithium cations flow through the electrolyte and the electrons, on the other hand, flow through a working resistance from the anode material to the cathode material.

To avoid a short circuit within the electrochemical cell, an electrically insulating layer through which, however, lithium cations can pass is located between the two electrodes. This can be a solid electrolyte or an ordinary separator.

Solid electrolytes and separators comprise, as is known, a support material into which a dissociable compound comprising lithium cations to increase the lithium ion conductivity and usually further additives such as solvents are incorporated.

As support material, U.S. Pat. No. 5,296,318 and U.S. Pat. No. 5,429,891 propose, for example, a copolymer of vinylidene fluoride and hexafluoropropene. However, the use of such high-resistance (co)polymers suffers from a series of disadvantages.

Such polymers are not only expensive but are also difficult to bring into solution. Furthermore, owing to their comparatively low lithium cation conductivity, they increase the resistance of the cell so that the electrolyte, which usually comprises a compound comprising lithium cations, e.g. $LiPF_6$, $LiAsF_6$ or $LiSbF_6$ and an organic solvent such as ethylene carbonate or propylene carbonate, was added during production of the insulating layer (U.S. Pat. No. 5,296,318, U.S. Pat. No. 5,429,891). In addition, such polymers can be processed only in the presence of, for example, high proportions of plasticizers, e.g. di-n-butylphthalate, and of pyrogenic silicas which are added, firstly, to ensure that the electrolyte layer is sufficiently film-forming and cohesive and can be adhesively bonded to the electrode layers and, secondly, to ensure sufficient conductivity and permeability for lithium cations. The plasticizer then has to be removed quantitatively from the laminar assembly of anode, solid electrolyte or separator layer and cathode layer before use of the batteries by means of an extraction step which is quite difficult and expensive on an industrial scale.

WO97/37397 relates, inter alia, to a mixture Ia comprising a mix IIa which comprises
a) from 1 to 95% by weight of a solid III, preferably a basic solid III, having a primary particle size of from 5 nm to 20 μm and
b) from 5 to 99% by weight of a polymeric composition IV obtainable by polymerization of
b1) from 5 to 100% by weight, based on the composition IV, of a condensation product V of
a) at least one compound VI which is able to react with a carboxylic acid or a sulfonic acid or a derivative thereof or a mixture of two or more thereof, and
b) at least 1 mol per mole of the compound VI of a carboxylic acid or sulfonic acid VII which has at least one freeradically polymerizable functional group, or a derivative thereof or a mixture of two or more thereof and
b2) from 0 to 95% by weight, based on the composition IV, of a further compound VIII having a mean molecular weight (number average) of at least 5000 and having polyether segments in a main or side chain, where the proportion by weight of the mix Ia in the mixture Ia is from 1 to 100% by weight.

Although the systems described there have excellent properties, particularly when used in electrochemical cells, for example excellent short-circuit resistance, high mechanical stability and good processability, when using these systems it is usually necessary to carry out the actual film production or the photocrosslinking step in the production of, for example, cast films under inert gas conditions.

It is an object of the present invention to provide a further improved system for use in electrochemical cells. In particular, it is an object of the present invention to provide a composition which can be processed more readily, i.e. with avoidance of inert gas conditions.

We have found that this object is achieved by a composition comprising:

(a) from 1 to 99% by weight of a pigment (I) having a primary particle size of from 5 nm to 100 μm which is a solid Ia or a compound Ib which acts as cathode material in electrochemical cells or a compound Ic which acts as anode material in electrochemical cells or a mixture of the solid Ia with the compound Ib or the compound Ic, (b) from 1 to 99% by weight of a polymeric material (II) which comprises:

(IIa) from 1 to 100% by weight of a polymer or copolymer (IIa) which has, as part of the chain, at the end(s) of the chain and/or laterally on the chain, reactive groups (RG) which are capable of crosslinking reactions under the action of heat and/or UV radiation, and (Ib) from 0 to 99% by weight of at least one polymer or copolymer (IIb) which is free of reactive groups RG.

In particular, this composition is notable for the novel crosslinker system (polymer IIa).

The pigment I can be a solid Ia. Advantageously, the solids are very largely insoluble in the liquid used as electrolyte and are electrochemically inert in the battery medium. The term "solid" as used within in the present invention, stands for all compounds which are present as solids under normal conditions, which, during use of the battery, neither take up nor emit electrons under the conditions which exist when loading batteries, particularly lithium ion batteries. Preferably, it is a solid which is selected from the group consisting of an inorganic solid, preferably a basic inorganic solid, selected from the group consisting of oxides, mixed oxides, carbonates, silicates, sulfates, phosphates, amides, imides, nitrides and carbides of the elements of main groups I., II., III. and IV. and transition group IV. of the Periodic Table; a polymer selected from the group consisting of polyethylene, polypropylene, polystyrene, polytetrafluoroethylene, polyvinylidene fluoride, polyamides, polyimides; a solids dispersion comprising such a polymer; glass powder, nanosize glass particles such as Monosper® (Merck), glass microparticles such as Spheriglas® (Potters-Ballotini), nanosize whiskers and a mixture of two or more thereof, so as to give a composition which can be used as solid electrolyte and/or separator.

Specific examples are: oxides such as silicon dioxide, aluminum oxide, magnesium oxide or titanium dioxide, mixed oxides, for example of the elements silicon, calcium, aluminum, magnesium, titanium; silicates such as ladder, chain, sheet and framework silicates, e.g. talc, pyrophyllite, muskovite, phlogopite, amphiboles, nesosilicates, pyroxenes, sorosilicates, zeolites, feldspars, wollastonite, in particular hydrophobicized wollastonite, mica, phyllosilicates; sulfates, such as alkali metal and alkaline earth metal sulfates; carbonates, for example alkali metal and alkaline earth metal carbonates such as calcium, magnesium or barium carbonate or lithium, potassium or sodium carbonate; phosphates, for example apatites; amides; imides; nitrides; carbides; polymers such as polyethylene, polypropylene, polystyrene, polytetrafluoroethylene, polyvinylidene fluoride, polyamides, polyimides or other thermoplastics, thermosets or microgels, crosslinked polymer particles such as Agfaperl®, solids dispersions, in particular those comprising the abovementioned polymers, and also mixtures of two or more of the abovementioned solids.

In addition, inorganic solids which conduct Li ions, preferably a basic inorganic solid which conducts Li ions, can be used according to the present invention as inert solid Ia.

Examples which may be mentioned are: lithium borates such as $Li_4B_6O_{11}*xH_2O$, $Li_3(BO_2)_3$, $Li_2B_4O_7*xH_2O$, $LiBO_2$, where x can be from 0 to 20; lithium aluminates such as $Li_2O*Al_2O_3*H_2O$, $Li_2Al_2O_4$, $LiAlO_2$; lithium aluminosilicates such as lithium-containing zeolites, feldspars, feldspar-like compounds, phyllosilicates and inosilicates, and, in particular $LiAlSi_2O_6$ (spodumene), $LiAlSi_4O_{10}$ (petullite), $LiAlSiO_4$ (eucryptite), mica, e.g. $K[Li,Al]_3[AlSi]_4O_{10}$ $(F—OH)_2$, $K[Li,Al,Fe]_3[AlSi]_4O_{10}(F—OH)_2$; lithium zeolites, in particular those in fiber, layer or cube form, especially those having the formula $Li_{2/z}O*Al_2O_3*xSiO_2*yH_2O$ where z corresponds to the valence, x is from 1.8 to about 12 and y is from 0 to about 8; lithium carbides such as $Li_2C_2$, $Li_4C$; $Li_3N$; lithium oxides and mixed oxides such as $LiAlO_2$, $Li_2MnO_3$, $Li_2O$, $Li_2O_2$, $Li_2MnO_4$, $Li_2TiO_3$; $Li_2NH$; $LiNH_2$; lithium phosphates such as $Li_3PO_4$, $LiPO_3$, $LiAlFPO_4$, $LiAl(OH)PO_4$, $LiFePO_4$, $LiMnPO_4$; $Li_2CO_3$; lithium silicates in ladder, chain, sheet and framework form, e.g. $Li_2SiO_3$, $Li_2SiO_4$ and $Li_6Si_2$; lithium sulfates such as $Li_2SO_4$, $LiHSO_4$, $LiKSO_4$; and also the Li compounds mentioned as compound Ib, with the presence of conductive carbon black being excluded when used as solid Ia; and also mixtures of two or more of the abovementioned solids which conduct Li ions.

As solid Ia, preference is given to using hydrophobicized solids Ia, more preferably hydrophobicized compounds of the abovementioned type.

Particularly suitable solids Ia are basic solids. For the purposes of the present invention, basic solids are ones whose mixture with a liquid, water-containing diluent, which itself has a pH of not more than 7, has a higher pH than this diluent.

The present invention further relates to a composition in which the pigment I is a compound Ib which acts as cathode material in electrochemical cells and is selected from the group consisting of $LiCoO_2$, $LiNiO_2$, $LiNi_xCo_yO_2$, $LiNi_xCo_yAl_zO_2$, where $0<x,y,z \leq 1$, $Li_xMnO_2$ $(0<x\leq 1)$, $Li_xMn_2O_4$ $(0<x\leq 2)$, $Li_xMoO_2$ $(0<x\leq 2)$, $Li_xMnO_3$ $(0<x\leq 1)$, $Li_xMnO_2$ $(0<x\leq)$, $Li_xMn_2O_4$ $(0<x\leq 2)$, $Li_xV_2O_4$ $(0<x\leq 2.5)$, $Li_xV_2O_3$ $(0<x\leq 3.5)$, $Li_xVO_2$ $(0<x\leq 1)$, $Li_xWO_2$ $(0<x\leq 1)$, $Li_xWO_3$ $(0<x\leq 1)$, $Li_xTiO_2$ $(0<x\leq 1)$, $Li_xTi_2O_4$ $(0<x\leq 2)$, $Li_xRuO_2$ $(0<x\leq 1)$, $Li_xFe_2O_3$ $(0<x\leq 2)$, $Li_xFe_3O_4$ $(0<x\leq 2)$, $Li_xCr_2O_3$ $(0<x\leq 3)$, $Li_xCr_3O_4$ $(0<x\leq 0.8)$, $Li_xV_3S_5$ $(0<x\leq 1.8)$, $Li Ta_2S_2$ $(0<x\leq 1)$, $Li_xFeS_2$ $(0<x\leq 1)$, $Li_xFeS_2$ $(0<x\leq 1)$, $Li NbS_2$ $(0<x\leq 2.4)$, $Li_xMoS_2$ $(0<x\leq 3)$, $Li_xTiS_2$ $(0<x\leq 2)$, $Li ZrS_2$ $(0<x\leq)$, $Li_xNbSe_2$ $(0<x\leq 3)$, $Li_xVSe_2$ $(0<x\leq 1)$, $Li NiPS_2$ $(0<x\leq 1.5)$, $Li_xFePS_2$ $(0<x\leq 1.5)$, $LiNi_xB_{1-x}O_2$ $(0<x\leq 1)$, $LiNi_xAl_{1-x}O_2$ $(0<x\leq 1)$, $LiNi_xMg_{1-x}O_2$ $(0<x\leq 1)$, $LiNi Co_{1-x}VO_4$ $(1>x>0)$, $LiNi_xCo_yMn_zO_2$ $(x+y+z=1)$, $LiFeO_2$, $LiCrTiO_4$, $Li_aM_bL_cO_d$ $(1.15\geq a>0; 1.3\geq b+c\geq 0.8; 2.5\geq d\geq 1.7$; M=Ni, Co, Mn; L=Ti, Mn, Cu, Zn, alkaline earth metal), $LiCu_x^{II}Cu_y^{III}Mn_{(2-(x+y))}O_4$ $(2>x+y>0)$, $LiCrTiO_4$, $LiGa_xMn_{2-x}O_4$ $(0.1\geq x\geq 20)$, poly(carbon sulfides) of the structure: $—[C(S_x)]_n—$, $V_2O_5$, a mixture of two or more thereof, and a mixture of compound Ib with the solid Ia, and the composition further comprises from 0.1 to 20% by weight, based on the total weight of components I and II, of conductive carbon black, giving a composition which can be used, in particular, as cathode.

In addition, the present invention provides a composition in which the pigment I is a compound Ic which acts as anode material in electrochemical cells and is selected from the group consisting of lithium, a lithium-containing metal alloy, micronized carbon black, natural and synthetic graphite, synthetically graphitized carbon powder, a carbon fiber, titanium oxide, zinc oxide, tin oxide, molybdenum oxide, tungsten oxide, titanium carbonate, molybdenum carbonate, zinc carbonate, $Li_xM_ySiO_z$ $(1>x>0.1>y>0, z>0)$, $Sn_2BPO_4$, conjugated polymers such as polypyrroles, polyanilines, polyacetylenes, polyphenylenes, lithium metal compounds $Li_xM$, such as those in which M=Sn, Bi, Sb, Zn, Cd, Pb and $5 \geq x \geq 0$; Li—Sn—Cd, CdO, PbO, a mixture of two or more thereof or a mixture of the compound Ic with the solid Ia, and the composition further comprises up to 20% by weight, based on the total weight of the components I and II, of conductive carbon black, giving a composition which can be used, in particular, as anode.

Particularly suitable pigments I are those which have a primary particle size of from 5 nm to 20 μm, preferably from 0.01 to 10 pm and in particular from 0.1 to 5 μm, where the particle sizes indicated are determined by electron microscopy. The melting point of the pigments is preferably above the operating temperature customary for the electrochemical cell, with melting points above 120° C., in particular above 150° C., having been found to be particularly useful.

The pigments can have a symmetric external shape, i.e. have a ratio of height: width: length (aspect ratio) of about 1 and be in the form of spheres, granules, approximately round structures, or in the form of any polyhedra, e.g. as cuboids, tetrahedra, hexahedra, octahedra or as bipyramids, or can have a distorted or asymmetric shape, i.e. have a ratio of height: width: length (aspect ratio) which is different from 1 and be in the form of, for example, needles, asymmetric tetrahedra, asymmetric bipyramrids, asymmetric hexahedra or octahedra, platelets, disks or fibrous structures. If the solids are in the form of asymmetric particles, the above-indicated upper limit for the primary particle size is based on the smallest axis in each case.

The composition of the present invention comprises from 1 to 95% by weight, preferably from 25 to 90% by weight, more preferably from 50 to 85% by weight, in particular from 65 to 80% by weight, of a pigment I and from 5 to 99% by weight, preferably from 10 to 75% by weight, more preferably from 15 to 50% by weight, in particular from 20 to 35% by weight, of the polymeric binder II.

This polymeric binder II comprises from 1 to 100% by weight of at least one polymer IIa which has, as part of the chain, at the end(s) of the chain and/or laterally on the chain, reactive groups (RG) which are capable of crosslinking reactions under the action of heat and/or UV radiation, and from 0 to 99% by weight of at least one polymer or copolymer (IIb) which is free of reactive groups RG.

As polymers IIa, it is in principle possible to use all polymers which are crosslinkable thermally and/or under high-energy radiation, preferably under UV light, and have, as part of the chain, at the end(s) of the chain and/or laterally on the chain, reactive groups (RG), preferably reactive groups RGa or RGb or RGa and RGb, via which the polymers can crosslink under the action of heat and/or radiation.

More preferably, the polymer IIa is a polymer which has, in each case as part of the chain, at the end(s) of the chain and/or laterally on the chain, at least one first reactive group RGa and at least one group RGb which is different from RGa and is coreactive with RGa, with at least one RGa and at least one RGb being present on average over all polymer molecules.

The oligomeric and/or polymeric base structure of the polymers IIa includes known polymers as are, for example, built up by means of —C≡C— linkages, which can also contain double and/or triple bonds, and also by means of ether, ester, urethane, amide, imide, imidazole, ketone, sulfide, sulfone, acetal, urea, carbonate and siloxane linkages.

Furthermore, the oligomeric or polymeric base structure can be linear, branched, cyclic or dendrimetric.

The polymers IIa used according to the present invention can be obtained by polymerization, polyaddition or polycondensation of monomeric building blocks which have RGa and/or RGb in addition to the groups via which polymer formation occurs, so that polymers IIa which are functionalized in accordance with the present invention are formed straightaway in the preparation of the polymers.

The polymers IIa used according to the present invention can also be obtained by polymer-analogous reaction of functional polymers with compounds having RGa and/or RGb and at least one further group which can react with the functional groups of the oligomeric or polymeric base structure.

It is also possible to incorporate one of the functional groups RGa and/or RGb in the preparation of the polymer and then to introduce the other RG into the finished polymer by polymer-analogous func-tionalization.

Groups RGa are groups having structures which, under high-energy radiation, preferably TV light, are capable, in the excited triplet state, of abstracting hydrogen (photoinitiator groups of the Norrish II type known from the literature). Such structures are known to those skilled in the art of photochemistry. Furthermore, the acrylate (derivative) compounds which have such structures are listed here. Further details of these compounds may be found in U.S. Pat. No. 5,558,911, whose full relevant contents are incorporated by reference into the present application. Of course, it is also possible, according to the present invention, to use other monomers, oligomers or polymers which contain such structures RGa.

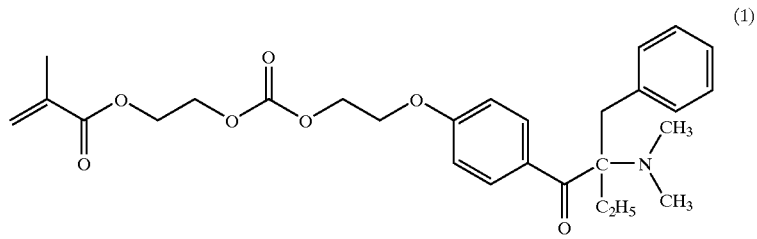

(1)

The polymer IIa can also be formed by a mixture of a plurality of polymers of which some have only RGa and others have only RGb.

The polymer Ia can also be formed by a mixture of a plurality of polymers of which some have only RGa and others have only RGb and further polymers which have both RGa and RGb.

In general, the polymer Ia is made up of a uniform polymer class, preferably the class of polyacrylates. However, blends of various polymer classes are also possible.

The polymer Ia includes both polymeric and oligomeric materials and also mixtures of polymeric and oligomeric materials.

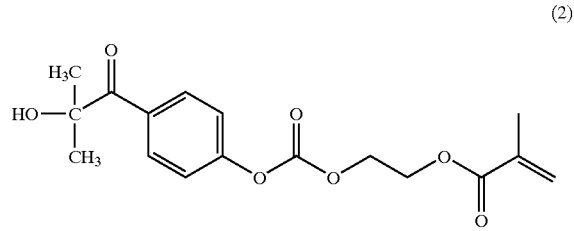

(2)

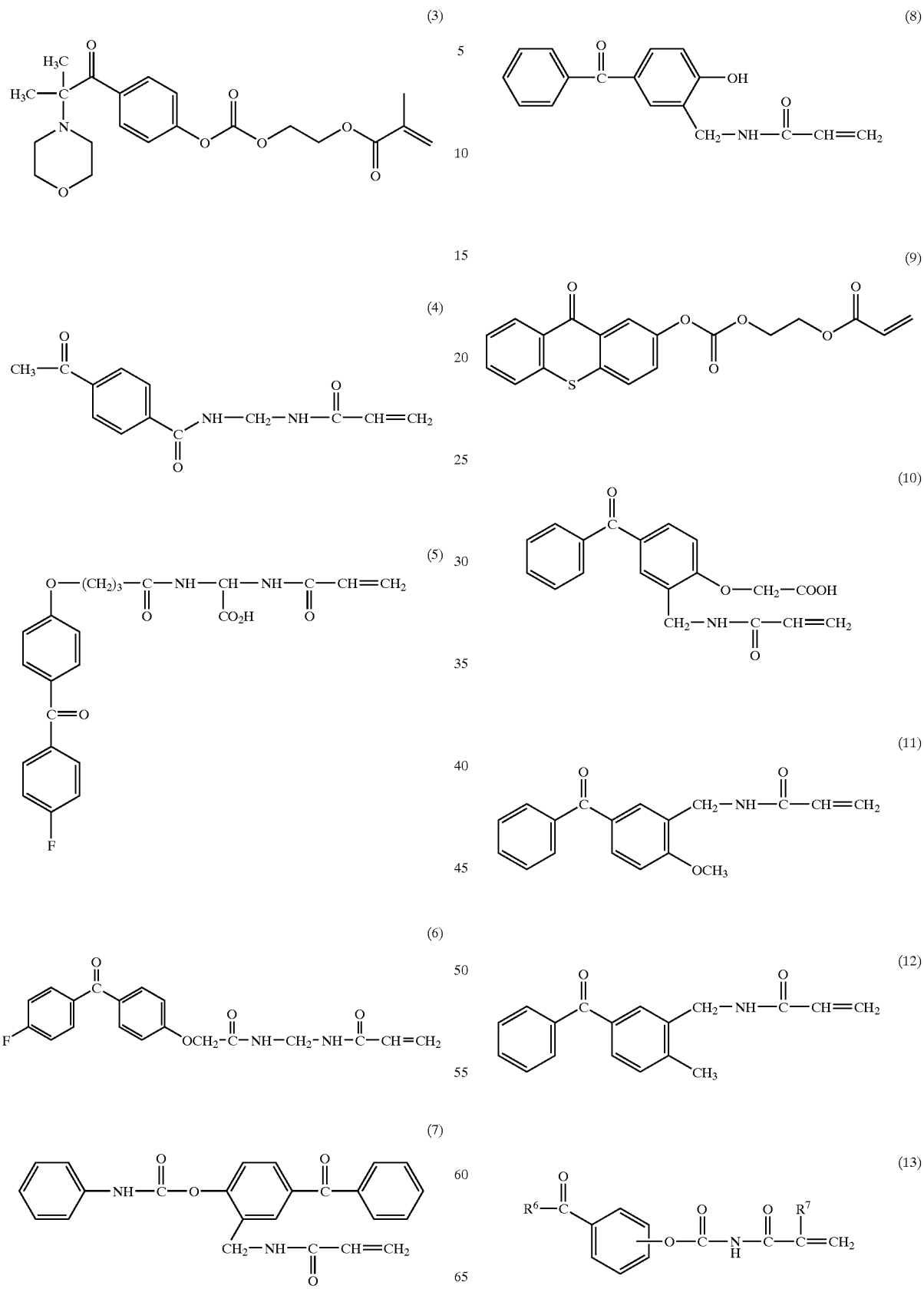

wherein
R⁶ is —CH₃ or —C₆H₅
R⁷ is —H or —CH₃
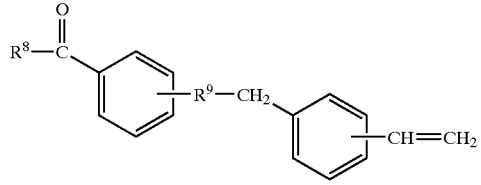
(14)
wherein
R⁸ is —$C_nC_{2n+1}$ with n=1 to 3 or —C₆H₅
R⁹ is —O—,
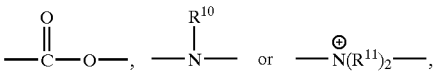
R¹⁰ is —H or —$C_nH_{2n-1}$ with n=1 to 8, and
R¹¹ is —$C_nH_{2n-1}$ with n=1 to 4
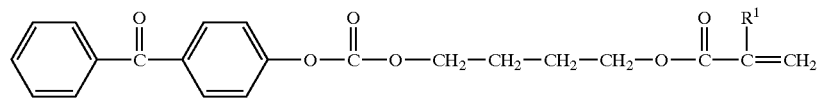
(15)
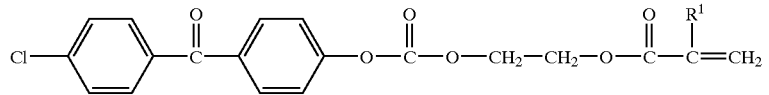
(16)
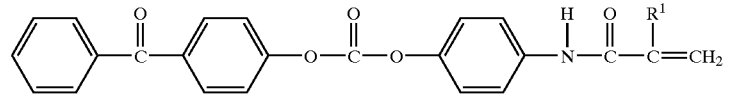
(17)
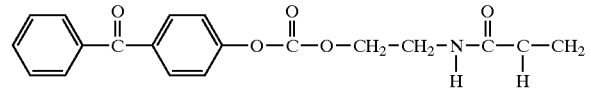
(18)
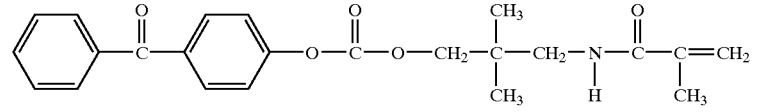
(19)

(20)
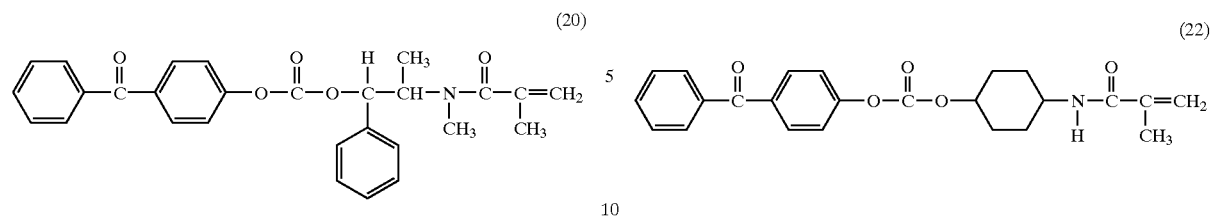
(21)
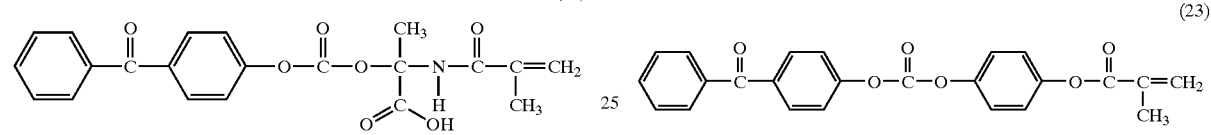
(22)
(23)
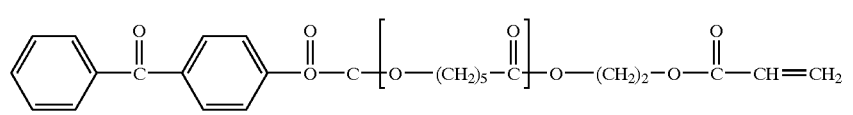
(24)
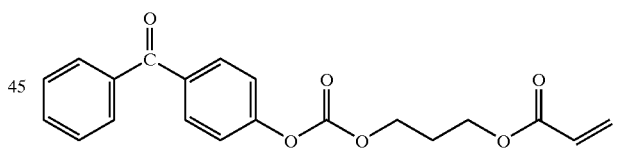
(25)
(26)
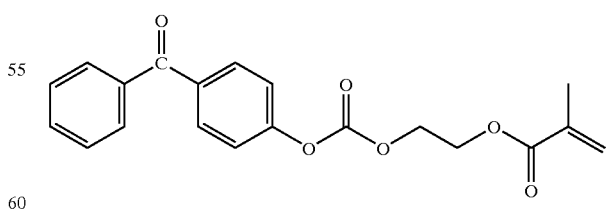

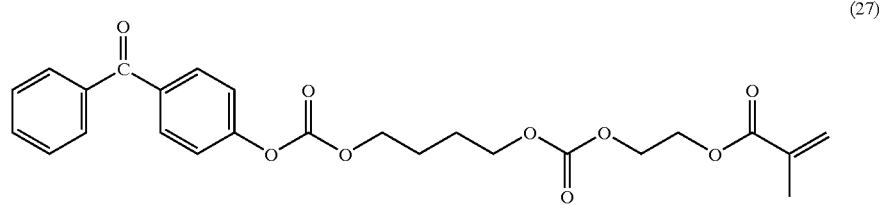
(27)
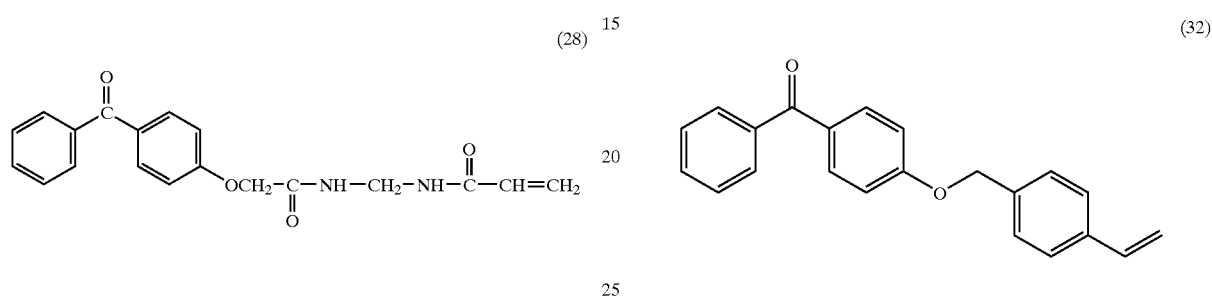
(28)
(32)
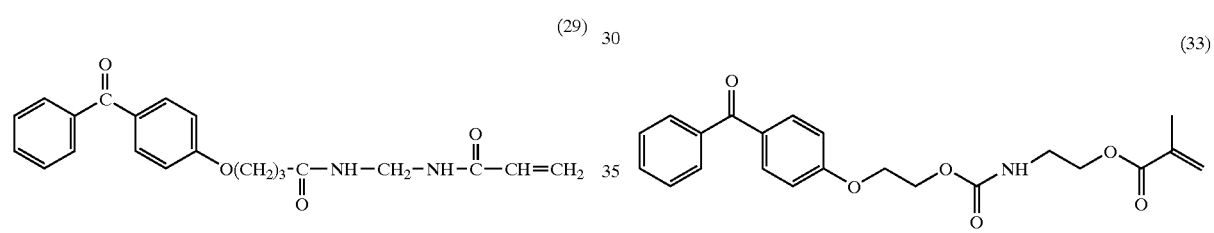
(29)
(33)
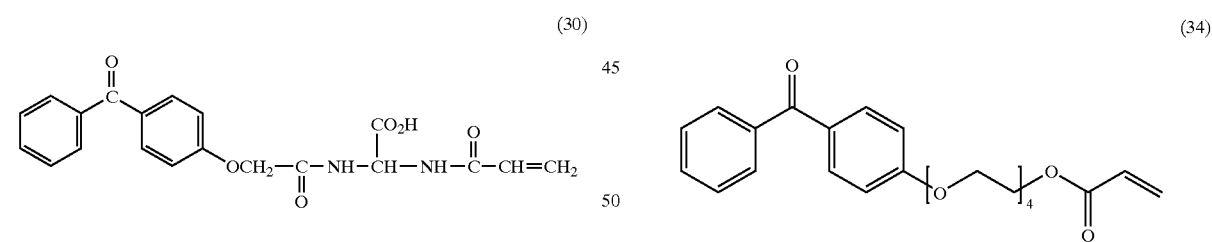
(30)
(34)
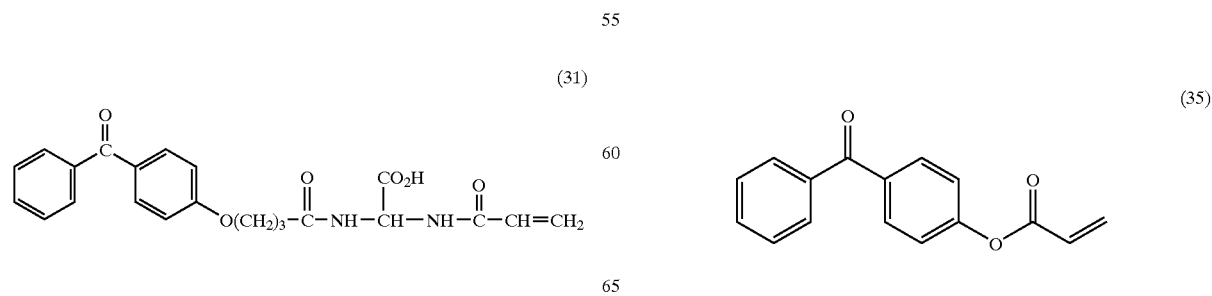
(31)
(35)

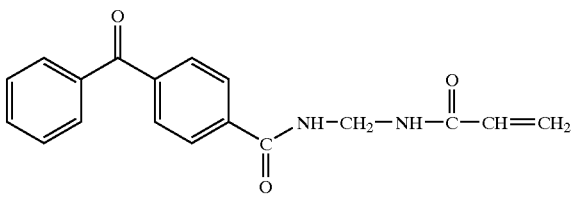
(36)

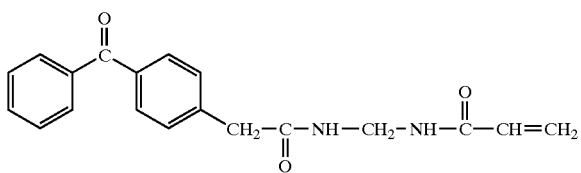
(37)

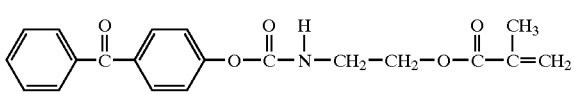
(38)

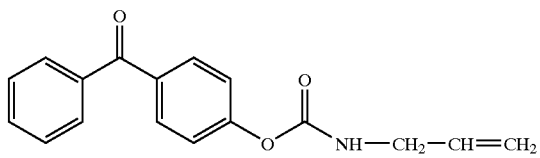
(39)

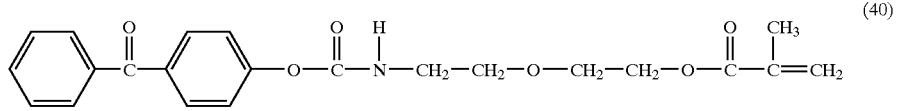
(40)

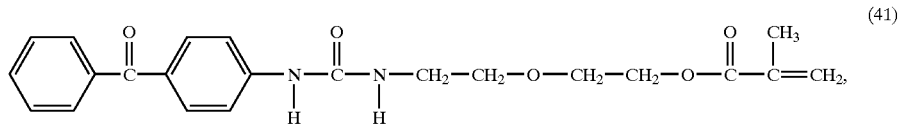
(41)

wherein $R^1$ is H or $CH_3$.

The concomitant use of such RGa-acrylates makes it readily possible, for example by copolymerization with further acrylates, to obtain acrylate copolymers which are functionalized by RGa in accordance with the present invention.

Furthermore, base polymers containing, for example, amino groups but no groups RGa can be readily functionalized by RGa via a Michael addition of such RGa-acrylates.

Preferred groups RGa are benzophenone groups. A particularly high UV reactivity is achieved in the case of polyacrylates comprising benzophenone derivatives in which the benzophenone group is bound to the main polymer chain via a spacer group. Particularly preferred polyacrylates are obtainable by copolymerization with acrylates of the formulae 24 to 26 and the formula 34.

A further inexpensive and preferred way of introducing RGa into polymers is the reaction of hydroxybenzophenones, preferably 4-hydroxybenzophenone, with the epoxide groups of a polymer, preferably the addition of 4-hydroxybenzophenone onto polyacrylates containing a proportion of glycidyl (meth)acrylate. A further elegant method is the reaction of an adduct of 1 mol of diisocyanate and 1 mol of 4-hydroxybenzophenone with a polymer having free hydroxyl groups.

A preferred method of introducing RGa into polyesters comprises the concomitant use of benzophenone carboxylic acids or benzophenonecarboxylic anhydrides in the polycondensation or the reaction or esterification of polymers containing hydroxyl groups, epoxide groups, isocyanate groups and/or amino groups with benzophenone carboxylic acids or benzophenone carboxylic anhydrides.

Groups RGb are groups which can interact with excited Norrish II photoinitiator groups. A particular interaction of this type known to those skilled in the art is the transfer of hydrogen to the Norrish II structure, resulting in formation of free radicals, both in the case of the H donor and in the case of the abstracting Norrish II structure. Combination of free radicals makes direct crosslinking of the polymers possible. Furthermore, the initiation of a free-radically initiated polymerization is also possible. A free-radically initiated polymerization of, for example, polymerizable functional groups RGb, e.g. maleate, fumarate, (meth)acrylate, allyl, epoxide, alkenyl, cycloalkenyl, vinyl ether, vinyl ester, vinyl aryl and cinnamate groups, can also be initiated by the photochemically generated free radicals.

Preference is given to RGb which interact as H donor with RGa, i.e. systems which are free of double bonds. An advantage inherent in such systems is the low sensitivity to interference of the systems because they have, compared to unsaturated UV systems, a reduced reactivity toward the further constituents of the overall formulation. Of course, this does not rule out the (concomitant) use of unsaturated materials and an optimization procedure for the individual case. H-donor groups are known to those skilled in the art of photochemistry. They are, in principle, groups which have hydrogen atoms having a low binding energy, particularly groups containing hydrogen atoms having a binding energy of less than 397 kJ/mol.

Values of binding energies are known from the literature and may be found, for example, in Morrison, Robert Thornton Organic Chemistry, Table: Homolytic Bond Dissociation Energies on the inside of the cover, in Library of Congress Cataloging-in-Publication Data ISBNO-205-08453-2, 1987, by Allyn and Bacon, Inc. A Division of Simon & Schuster, Newton, Mass., USA.

Examples are amine, furfuryl, tetrahydrofurfuryl, isobornyl, and isoalkyl compounds and compounds which have groups of the following structures:

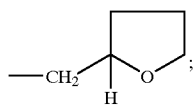

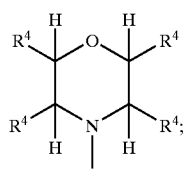

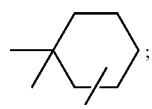

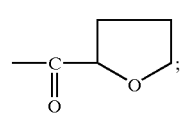

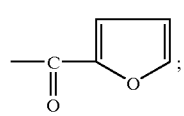

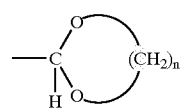

(n=2 oder 3);

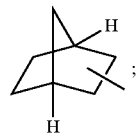

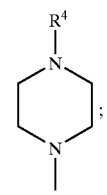

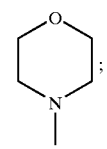

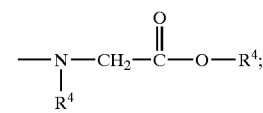

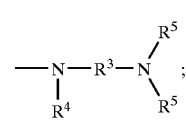

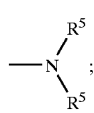

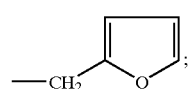

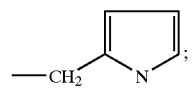

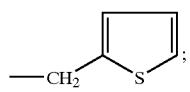

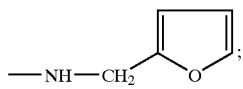

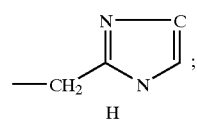

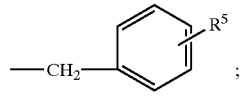

wherein R³=a divalent aliphatic, cycloaliphatic, heterocyclic or aromatic residue, that residue being optionally substituted, or a single bond;
R⁴=H, linear or branched alkyl, e.g. having one 1 to 8 carbon atoms, halogen substituted aryl or isoamylphenyl;
R⁵=alkyl, halogen substituted alkyl, halogen substituted aryl or isoamylphenyl. These formulae are examples only and do not constitute a restriction.

Preference is given to groups of this type which have, as readily abstractable H atoms, H atoms in the α position to a double bond (allylic H atoms). As RGb, particular preference is given to groups RGb1

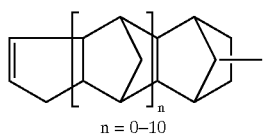

Ways of incorporating such structures are, for example, the concomitant use of the ester of (oligo)-dihydrodicyclopentadienol.

RGb2

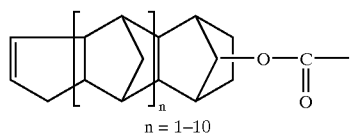

The maleate/fumarate monoesters of (oligo)-dihydrodicyclopentadienol are readily obtainable industrially from maleic acid and DCPD.

These monoesters are obtainable in a smooth reaction from maleic anhydride (MA), water and dicyclopentadiene (DCPD) or by direct addition of DCPD onto MA. It is also possible to add DCPD directly onto other acids and/or acidic polyesters. However, these reactions usually do not proceed as readily and require catalysis, e.g. by BF₃ etherate.

RGb3

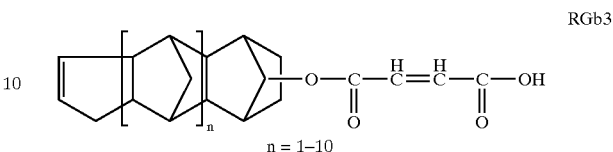

n = 1–10

Furthermore, it is known, for example, from U.S. Pat. No. 252,682 that secondary reactions according to the following reaction scheme can take place to a subordinate extent in the reaction of DCPD and MA. These by-products likewise serve to introduce structures of the formula RGb 1.

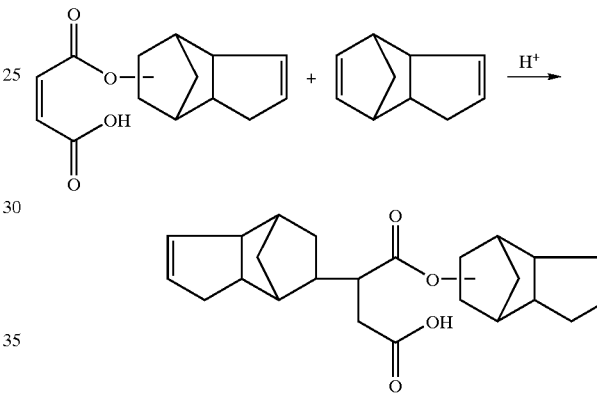

Furthermore, dihydrodicyclopentadienol and dihydro-dicyclopentadienyl acrylate are commercially available and suitable for introducing the particularly preferred RG b) structures.

RGb4

RGb5

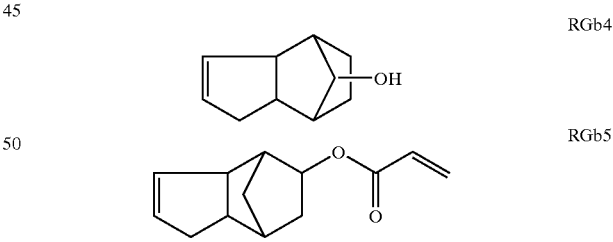

Hydroxy-functional compounds for introducing groups of the formula RGb1 are dihydrodicyclopentadienyl alcohol and preferably the adducts of DCPD and glycols which are obtainable in an inexpensive way in the presence of acid catalysts according to the reaction scheme below

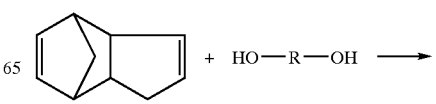

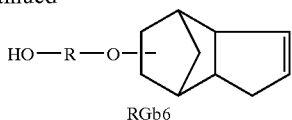
RGb6

Further groups RGb which are of interest are endomethylenetetrahydrophthalic acid structures which are obtainable, for example, by addition of CPD onto maleate groups.

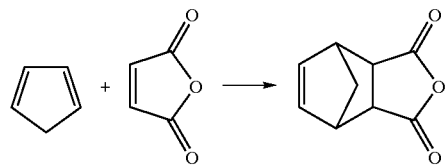

The introduction of endomethylenetetrahydrophthalic acid structures by addition of CPD onto the double bonds of unsaturated polyesters is of particular interest.

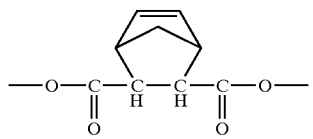

Also of interest is the introduction of endomethylenetetrahydrophthalic acid and tetrahydrophthalic acid structures via the imides of these acids with hydroxyalkylamines, as are known, for example, from DE-A-15700273 or DE-A17200323.

The oligomeric and/or polymeric base structure of the polymers IIa includes the known polymers as are, for example, built up by —C≡C— linkages, which can also have double and/or triple bonds, and by ether, ester, urethane, amide, imide, imidazole, ketone, sulfide, sulfone, acetal, urea, carbonate and siloxane linkages, subject to the proviso of the functionalizations which have been more precisely defined above.

Preference is given to using polyesters, polyethers, polyurethanes and, particularly preferably, polyacrylates.

For the purposes of the present invention, polyesters are saturated and unsaturated polyester resins.

To prepare the polyester resins, it is possible to use the customary and known carboxylic acids having ≧2 carboxyl groups and/or their anhydrides and/or their esters and hydroxyl compounds having ≧2 OH groups. Concomitant use can also be made of monofunctional compounds, for example to regulate the molecular weight of the polycondensates.

Suitable carboxylic acid components are, for example, α,β-ethylenically unsaturated carboxylic acids such as maleic acid, maleic anhydride, fumaric acid, itaconic acid, citraconic acid, saturated aliphatic carboxylic acids or their anhydrides, e.g. succinic acid, adipic acid, suberic acid, sebacic acid, azelaic acid, natural fatty acids and polymerized natural fatty acids, e.g. leinoleic acid and dimeric and polymeric leinoleic acid, castor oil, ricinoleic acid, saturated cycloaliphatic carboxylic acids or their anhydrides, e.g. tetrahydrophthalic acid, hexahydrophthalic acid, endomethylenetetrahydrophthalic acid, norbornene dicarboxylic acid, aromatic carboxylic acids or their anhydrides, e.g. phthalic acid in its isomeric forms, also tricarboxylic and tetracarboxylic acids or their anhydrides, e.g. trimellitic acid, pyromellitic acid, polycarboxylic acids which have been partially esterified by allyl alcohol, e.g. monoallyl trimellitate or diallyl pyromellitate, with benzophenonecarboxylic acids being of particular importance because these copolymers enable UV-excitable structures to be incorporated.

Possible hydroxyl components are, for example, alkoxylated or unalkoxylated, at least dihydric aliphatic and/or cycloaliphatic alcohols such as ethylene glycol, propylene glycol, polyethylene glycols, polypropylene glycols, butanediol isomers, hexanediol, trimethylolpropane, pentaerythritol, neopentyl glycol, cyclohexanedimethanol, bisphenol A, hydrogenated bisphenol A, OH-polyfunctional polymers such as hydroxyl-modified polybutadienes or hydroxyl-bearing polyurethane prepolymers, glycerol, monoglycerides and diglycerides of saturated and unsaturated fatty acids, in particular monoglycerides of linseed oil or sunflower oil. Furthermore, it is also possible to use unsaturated alcohols such as polyfunctional hydroxyl compounds which have been (partially) etherified by allyl alcohol, e.g. trimethylolethane monoallyl ether, trimethylolethane diallyl ether, trimethylolpropane monoallyl ether, trimethylolpropane diallyl ether, pentaerythritol monoallyl ether or pentaerythritol diallyl ether, 2-butene-1,4-diol and alkoxylated 2-butene-1,4-diol.

If monofunctional substances are used for regulating the molecular weight, these are preferably monofunctional alcohols such as ethanol, propanol, butanol, hexanol, decanol, isodecanol, cyclohexanol, benzyl alcohol or allyl alcohol. For the purposes of the present invention, the term polyesters includes polycondensates which have amide and/or imide groups in addition to the ester groups, as are obtained by concomitant use of amino compounds. Polyesters which have been modified in this way are known, for example from DE-A-15700273 and DE-A17200323. If endomethylenetetrahydrophthalic acid and tetrahydro-phthalic acid structures are introduced via the imides of these acids with hydroxyalkylamines as are mentioned there, these are groups RGb for the purposes of the present invention.

DCPD can also be added onto the double bonds of the unsaturated polyesters used, which makes it possible to incorporate endomethylenetetrahydrophthalic acid structures which represent groups RGb for the purposes of the present invention. These endomethylene-tetrahydrophthalic acid structures can be present on the internal double bonds of the polyesters and/or on terminal double bonds as have been introduced, for example, via substances of the formula 3. The double bonds from the unsaturated dicarboxylic acids and/or unsaturated diols are chain RGb groups for the purposes of the invention. The introduction of the RGs can be achieved by cocondensation and/or by polymer-analogous reactions on polyesters having functional groups. Examples of cocondensation are the concomitant use of trimethylolpropane diallyl and monoallyl ethers, pentaerythritol diallyl and monoallyl ethers, 2-butene-1,4-diol, alkoxylated 2-butene-1,4-diol, allyl alcohol and compounds of the formulae 3, 4, 5, 7, 8.

A preferred way of introducing RGa is the cocondensation of benzophenonecarboxylic acids or their anhydrides. Further preference is given to the addition of reaction products of hydroxybenzophenones with an excess of diisocyanates onto hydroxy-functional polyesters.

Groups RGb can also be introduced into hydroxy-functional polyesters in this way. For this purpose, diisocyanates having isocyanate groups of differing reactivity, e.g. isophorone diisocyanate or tolylene 1,4-diisocyanate, are preferably first reacted with half the stoichiometric amount of, for example, hydroxyacrylates, hydroxyvinyl ethers, hydroxyallyl esters, hydroxyallyl ethers or hydroxy-DCPD compounds of formulae AGb4 and AGb6 and these reaction products are then reacted with the hydroxy-functional polyesters. In the reactions mentioned, hydroxy-functional substances of different types can also be used at the same time.

Poly(meth)acrylate resins which are functionalized according to the present invention by RG represent a further important class of polymers to be used according to the present invention and are obtained by copolymerization of acrylic esters, with or without further copolymerizable compounds.

The poly(meth)acrylate resins used according to the present invention can also be prepared in solvents. A further advantageous method for preparing poly(meth)acrylates is the solvent-free, free-radical bulk polymerization in a stirred reactor, at atmospheric or superatmospheric pressure, or in continuous reactors at temperatures above the melting point of the polymers formed.

Suitable components for preparing poly(meth)acrylate resins are, for example, the known esters of acrylic acid and methacrylic acid with aliphatic, cycloaliphatic, araliphatic and aromatic alcohols having from 1 to 40 carbon atoms, for example methyl (meth)acrylate, ethyl (meth)acrylate, propyl (meth)acrylate, isopropyl (meth)acrylate, n-butyl (meth)acrylate, isobutyl (meth)acrylate, tert-butyl (meth)acrylate, amyl (meth)acrylate, isoamyl (meth)acrylate, hexyl (meth)acrylate, 2-ethylhexyl (meth)acrylate, decyl (meth)acrylate, undecyl (meth)acrylate, dodecyl (meth)acrylate, tridecyl (meth)acrylate, cyclohexyl (meth)acrylate, methylcyclohexyl (meth)acrylate, benzyl (meth)acrylate, tetrahydrofurfuryl (meth)acrylate, furfuryl (meth)acrylate and the esters of 3-phenylacrylic acid and their various isomeric forms, e.g. methyl cinnamate, ethyl cinnamate, butyl cinnamate, benzyl cinnamate, cyclohexyl cinnamate, isoamyl cinnamate, tetrahydrofurfuryl cinnamate and furfuryl cinnamate, acrylamide, methacrylamide, methylolacrylamide, methylolmethacrylamide, acrylic acid, methacrylic acid, 3-phenylacrylic acid, hydroxyalkyl (meth)acrylates such as ethylene glycol mono(meth)acrylate, butylene glycol mono(meth)acrylate and hexanediol mono(meth)acrylate, glycol ether (meth)acrylates such as methoxyethylene glycol mono(meth)acrylate, ethoxyethylene glycol mono(meth)acrylate, butoxyethylene glycol mono(meth)acrylate, phenoxyethylene glycol mono(meth)acrylate, glycidyl acrylate and glycidyl methacrylate, and amino (meth)acrylates such as 2-aminoethyl (meth)acrylate.

Further possible components are free radically copolymerizable monomers such as styrene, 1-methylstyrene, 4-tert-butylstyrene, 2-chlorostyrene, vinyl esters of fatty acids having from 2 to 20 carbon atoms, e.g. vinyl acetate and vinyl propionate, vinyl ethers of alkanols having from 2 to 20 carbon atoms, e.g. vinyl isobutyl ether, vinyl chloride, vinylidene chloride, vinyl alkyl ketones, dienes such as butadiene and isoprene and also esters of maleic and crotonic acids. Further suitable monomers are cyclic vinyl compounds such as vinylpyridine, 2-methyl-1-vinylimidazole, 1-vinylimidazole, 5-vinylpyrrolidone and N-vinylpyrrolidone. It is also possible to use allylically unsaturated monomers such as allyl alcohol, allyl alkyl esters, monoallyl phthalate and allyl phthalate. Acrolein and methacrolein and polymerizable isocyanates are also suitable.

The RGs can be incorporated by copolymerization in the preparation of the poly(meth)acrylates or by subsequent polymer-analogous reactions. Readily polymerizable compounds which have groups RGb are, for example, dihydrodicyclopentadienyl (meth)acrylate, dihydrocyclopentadienyl ethacrylate and dihydrodicyclopentadienyl cinnamate. Readily polymerizable compounds which have further groups on which a polymer-analogous functionalization is possible are, for example, copolymerizable epoxide compounds such as glycidyl (meth)acrylate or hydroxyalkyl (meth)acrylates. The hydroxyl and/or epoxide groups incorporated in this way are anchor groups for polymer-analogous functionalization reactions of the polymers. Epoxide groups are suitable, for example, for introducing acrylic double bonds by reaction with (meth)acrylic acid (RGb) and/or for introducing vinyl ether groups (RGb) by reaction with amino vinyl ether compounds such as diethanolamine divinyl ether or for introducing benzophenone groups (RGa) by reaction with hydroxybenzophenones and/or aminobenzophenones.

Polyurethanes which are functionalized according to the present invention by RG represent a further important class of polymers to be used according to the present invention and are obtained in a manner known to those skilled in the art from polyfunctional, usually bifunctional, isocyanates and polyhydroxy and/or polyamino compounds. Here too, it is possible to introduce RGa and/or RGb directly during the formation of the polyurethanes or subsequently into functional polyurethanes. The chemical reactants here are essentially the same ones as in the previously described polymers. RGa groups are preferably introduced by the concomitant use of functional benzophenone compounds and RGb groups are preferably introduced via hydroxy-DCPD compounds of the formulae RGb4 and RGb6.

Further details regarding the basic polyurethane structures which can be used may be found in the corresponding discussion of the polyurethanes which can be used as polymer IIb.

The preparation of polymers IIa to be used according to the invention is carried out in accordance with the generally known rules and is known to those skilled in the art of polymers, for example with regard to the setting of a desired molecular weight by concomitant use of regulating or monofunctional starting materials or the setting of a desired glass transition temperature by balancing of hard/soft components.

Compounds which are particularly suitable for introducing RGa into polymers IIa used according to the present invention, particularly into, as described above, epoxy- and/or hydroxy-functionalized polyesters, polyurethanes or polyacrylates, are:

2-, 3- and 4-hydroxybenzophenone, 2-hydroxy-5-methylhydroxybenzophenone, 2hydroxy-4-methoxybenzophenone, 2-hydroxy-4-octyloxybenzophenone, 2-hydroxy-4-dodecyloxybenzophenone, 2-hydroxy-5-chlorohydroxybenzophenone, 2-hydroxy-4-methoxy-4'-methylbenzophenone, 2-hydroxy-4-methoxy-4'-chlorobenzophenone, 4-hydroxy-3-methylbenzophenone, 4-hydroxy-4'-methoxybenzophenone, 4-hydroxy-4'-chlorobenzophenone, 4-hydroxy-4'-fluorobenzophenone, 4-hydroxy-4'-cyanobenzophenone, 4-hydroxy-2',4'-dimethoxybenzophenone, 2,2',4,4'- and 2,4-dihydroxybenzophenone, 4-tert-butyl-30 2,4-dihydroxybenzophenone, 2,2'-dihydroxy-4-methoxybenzophenone, 2,2'-dihydroxy-4-octoxybenzophenone, 2,2'-dihydroxy-4,4'-dimethoxybenzophenone, 2,4,4'-, 2,3,4- and 2,4,6-trihydroxybenzophenone, 2,2'-, 4,4'-, 2,3,4,4'- and 2,3',4,4'-tetrahydroxybenzophenone, 2-, 3- and 4-aminobenzophenone, 2-amino-4-methylbenzophenone, 2-amino-6-methylbenzophenone, 2-amino-4'-methylbenzophenone, 2-amino-4'-chloro-5-fluorobenzophenone, 2-amino-5-chlorobenzophenone, 2-amino-5-bromobenzophenone, 2-amino-5-methylbenzophenone, 2-amino-N-ethylbenzophenone, 2-amino-2',5'-dimethylbenzophenone, 4-amino-2-chlorobenzophenone, 4-amino-4'-methoxy-benzophenone, 3,4-, 4,4'- and 3,3'-diaminobenzophenone, 4,4'-bis(methylamino)benzophenone, 3,3',4,4'-tetraminobenzophenone, 2-, 3- and 4-benzoylbenzoic acid, 2-benzoyl-3'-methylbenzoic acid, 2-benzoyl-4'-ethylbenzoic acid, 2-benzoyl-3,6-dimethylbenzoic acid, 2-benzoyl-2',6'-dimethylbenzoic acid, 2-benzoyl-3',4'-dimethylbenzoic acid, 2-benzoyl-2',4',6-dimethylbenzoic acid, 2-benzoyl-p-hydroxybenzoic acid, 2-benzoyl-4'-methyl-3'-chlorobenzoic acid, 2-benzoyl-6-chlorobenzoic acid, 4-benzoyl-4'-isopropylbenzoic acid, 4-benzoyl-4'-chlorobenzoic acid, 4-benzoyl-4'-(2-carboxypropyl)benzoic acid, 2,4-, 3,4- and 4,4'-benzophenonedicarboxylic acid, 2',3,4-, 3,3',4- and 3,4,4'-benzophenonetricarboxylic acid, 3,3',4,4'-benzophenonetetracarboxylic acid and dianhydride, 2-hydroxy-4-methoxy-5-sulfobenzophenone, 4-(4-carboxy-phenyloxy)benzophenone, 4-(3,4-bis(carboxy)phenyloxy)benzophenone and the corresponding anhydride, 4'-(4-carboxyphenyloxy)benzophenone-4-carboxylic acid, 4'-(4-carboxyphenyloxy)benzophenone-3,4-dicarboxylic acid and the corresponding anhydride, 4'-(3,4-bis(carboxy)phenyloxy)benzophenone-2,4- and 3,4-dicarboxylic acid and the correspondidng anhydrides, 4-(4-cyanobenzoyl)thiophenol, 4-(2-hydroxyethoxy)phenyl 2-hydroxy-2-propyl ketone, 4-(2-aminoethoxy)phenyl 2-hydroxy-2-propyl ketone, 4-(2-hydroxycarbonylmethoxy)phenyl 2-hydroxy-2-propyl ketone, 4-(2-isocyanatomethoxy)phenyl 2-hydroxy-2-propyl ketone, 4-(2-isocyanatomethoxy)phenyl 2-hydroxy-2-propyl ketone, 2-([2-]6-isocyanatohexylaminocarbonyloxy)ethoxythioxanthone and phenylglyoxylic acid.

Furthermore, the polymers and copolymers discussed below under "polymers IIb" can also be used as polymers IIa as long as they are provided with reactive groups RG, in particular RGa and/or RGb. Particular mention may here be made of polymers and copolymers of halogen-containing olefinic compounds (group 4f)) which have been provided with reactive groups RG.

The crosslinking of the polymers IIa used according to the present invention is preferably carried out by means of high-energy radiation, in particular UV light. In most cases, no further addition of photoinitiator is necessary, i.e. the materials are self-photocrosslinking, and a particular advantage is their low inhibition by air. However, addition of further commercial photoinitiators is not ruled out. Furthermore, many polymers Ia are also thermally crosslinkable. Particularly high thermal crosslinkability is obtained in the presence of peroxides and/or C—C-labile substances of the benzopinacol type in the case of unsaturated systems which additionally have DCPD groups. Some of these systems can also be cured thermally in the absence of peroxides. Particularly rapid crosslinking is achieved e.g. by combined use of heat and UV light, e.g. by a combination of IR and UV sources.

As polymers IIb, use is made of thermoplastic and ion-conducting polymers. Particular mention may be made of:
1) homopolymers, copolymers or block copolymers (polymers IIb1) obtainable by polymerization of
   b1) from 5 to 100% by weight, based on the polymer IIb1, of a condensation product of
   a) at least one compound (a) which is able to react with a carboxylic acid or a sulfonic acid or a derivative thereof or a mixture of two or more thereof, and
   b) at least 1 mol per mole of this compound (a) of a carboxylic acid or sulfonic acid (b) which has at least one free-radically polymerizable functional group, or a derivative thereof or a mixture of two or more thereof and
   b2) from 0 to 95% by weight, based on the polymer IIb1, of a further compound (c) having a mean molecular weight (number average) of at least 5000 and having polyether segments in a main or side chain.

The polymer IIb1 is preferably obtainable by polymerization of
   b1) from 5 to 100% by weight, based on the polymer IIb1, of a condensation product of
   a) a polyhydric alcohol which contains carbon and oxygen atoms in the main chain, and
   b) at least 1 mol per mole of the polyhydric alcohol of an α,β-unsaturated carboxylic acid, and
   b2) from 0 to 95% by weight, based on the polymer IIb1, of a further compound (c) having a mean molecular weight (number average) of at least 5000 and having polyether segments in a main or side chain.

As compound (a), which is able to react with a carboxylic acid or a sulfonic acid (b) or a derivative thereof or a mixture of two or more thereof, it is in principle possible to use all compounds which meet this criterion and are free of reactive groups RG.

The compound (a) is preferably selected from the group consisting of a monohydric or polyhydric alcohol which has only carbon atoms in the main chain; a monohydric or polyhydric alcohol which in the main chain has at least two carbon atoms plus at least one atom selected from the group consisting of oxygen, phosphorus and nitrogen; a silicon-containing compound; an amine having at least one primary amino group; an amine having at least one secondary amino group; an aminoalcohol; a monohydric or polyhydric thiol; a compound containing at least one thiol group and at least one hydroxyl group; and a mixture of two or more thereof.

Among these, preference is in turn given to compounds (a) which have two or more functional groups capable of reacting with the carboxylic acid or sulfonic acid.

When compounds (a) containing amino groups as functional groups are used, preference is given to using those having secondary amino groups so that, after the condensation, no free NH groups, or only small numbers thereof, are present in the composition of the present invention.

Specific examples of preferred compounds (a) are:
monohydric or polyhydric alcohols which have only carbon atoms in the main chain and have from 1 to 20, preferably from 2 to 20 and in particular from 2 to 10, alcoholic OH groups, in particular dihydric, trihydric and tetrahydric alcohols, preferably having from 2 to 20 carbon atoms, e.g. ethylene glycol, 1,2- or 1,3-propanediol, 1,2- or 1,3-butanediol, 1,4-butenediol or 1,4-butynediol, 1,6-hexanediol, neopentyl glycol, 1,2-dodecanediol, glycerol, trimethylolpropane, pentaerythritol or sugar alcohols, hydroquinone, novolak, bisphenol A, although it is also possible to use, as indicated by the above definition, monohydric alcohols such as methanol, ethanol, propanol, n-, sec- or tert-butanol, etc.; use can also be made of polyhydroxyolefins, preferably those having two terminal hydroxyl groups, e.g. α,ω-dihydroxybutadiene;

polyester polyols as are known, for example, from *Ullmanns Encyklopädie der technischen Chemie*, 4th edition, vol. 19, pp. 62–65, and are obtained, for example, by reaction of dihydric alcohols with polybasic, preferably dibasic, polycarboxylic acids; monohydric or polyhydric alcohols which contain at least two carbon atoms plus at least one oxygen atom in the main chain, preferably polyether alcohols such as polymerization products of alkylene epoxides, for example isobutylene oxide, propylene oxide, ethylene oxide, 1,2-epoxybutane, 1,2-epoxypentane, 1,2-epoxyhexane, tetrahydrofuran, styrene oxide, with it also being possible to use polyether alcohols which have been modified at the end groups, e.g. polyether alcohols modified by $NH_2$ end groups; these alcohols preferably have a molecular weight (number average) of from 100 to 5000, more preferably from 200 to 1000 and in particular from 300 to 800; such compounds are known per se and are commercially available, for example under the trade names Pluriol® or Pluronic® (from BASF Aktiengesellschaft);

alcohols, as defined above, in which some or all carbon atoms are replaced by silicon, as which it is possible to use, in particular, polysiloxanes or alkylene oxide-siloxane copolymers or mixtures of polyether alcohols and polysiloxanes as are described, for example, in EP-B 581 296 and EP-A 525 728; as regards the molecular weight of these alcohols, what has been said above applies likewise;

alcohols, as defined above, in particular polyether alcohols, in which some or all oxygen atoms are replaced by sulfur atoms; as regards the molecular weight of these alcohols, what has been said above applies likewise;

monohydric or polyhydric alcohols which in the main chain contain at least two carbon atoms plus at least one phosphorus atom or at least one nitrogen atom, e.g. diethanolamine, triethanolamine;

lactones derived from compounds of the formula HO—$(CH_2)_z$—COOH, where z is from 1 to 20, e.g. ε-caprolactone, β-propiolactone, γ-butyrolactone or methyl-ε-caprolactone;

a silicon-containing compound such as dichlorosilane or trichlorosilane, phenyltri-chlorosilane, diphenyldichlorosilane, dimethylvinylchlorosilane; silanols such as trimethylsilanol;

an amine having at least one primary and/or secondary amino group, e.g. butylamine, 2-ethylhexylamine, ethylenediamine, hexamethylenediamine, diethylenetriamine, tetraethylenepentamine, pentaethylenehexamine, aniline, phenylenediamine;

polyetherdiamines such as 4,7-dioxydecane-1,10-diamine, 4,11-dioxytetradecane-1,14-diamine;

a monohydric or polyhydric thiol, for example aliphatic thiols such as methanethiol, ethanethiol, cyclohexanethiol, dodecanethiol; aromatic thiols such as thiophenol, 4-chlorothiophenol, 2-mercaptoaniline;

a compound containing at least one thiol group and at least one hydroxyl group, e.g. 4-hydroxythiophenol and also monothio derivatives of the above-defined polyhydric alcohols;

aminoalcohols such as ethanolamine, N-methylethanolamine, N-ethylethanolamine, N-butylethanolamine, 2-amino-1-propanol, 2-amino-1-phenylethanol;

monoamino or polyamino polyols having more than two aliphatically bound hydroxyl groups, e.g. tris(hydroxymethyl)methylamine, glucamine, N,N'-bis(2-hydroxyethyl)ethylenediamine, and mixtures thereof.

It is also possible to use mixtures of two or more of the above-described compounds (a).

The abovementioned compounds (a) are, according to the present invention, condensed with a carboxylic acid or sulfonic acid (b) which has at least one free-radically polymerizable functional group, or a derivative thereof or a mixture of two or more thereof, with at least one, preferably all, of the free groups capable of condensation in the compounds (a) being condensed with the compound (b).

As carboxylic acid or sulfonic acid (b) used for the purposes of the present invention, it is in principle possible to use any carboxylic and sulfonic acids which have at least one free-radically polymerizable functional group, and also derivatives thereof. The term "derivatives" used here includes both compounds which are derived from a carboxylic or sulfonic acid which has been modified at the acid function, e.g. esters, acid halides or acid anhydrides, and also compounds which are derived from a carboxylic or sulfonic acid which is modified on the carbon skeleton of the carboxylic or sulfonic acid, e.g. halocarboxylic or halosulfonic acids.

Particular examples of compound (b) are:

α,β-unsaturated carboxylic acids or β,γ-unsaturated carboxylic acids or derivatives thereof.

Particularly suitable α,β-unsaturated carboxylic acids are those of the formula

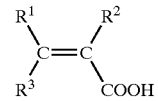

where $R^1$, $R^2$, $R^3$ and $R^3$ are hydrogen or $C_1$–$C_4$-alkyl radicals and among these acrylic acid and methacrylic acid are in turn preferred; also useful are cinnamic acid, maleic acid, fumaric acid, itaconic acid or p-vinylbenzoic acid, and also derivatives thereof, e.g. anhydrides such as maleic or itaconic anhydride; halides, in particular chlorides, such as acryloyl or methacryloyl chloride; esters such as (cyclo)alkyl (meth)acrylates having up to 20 carbon atoms in the alkyl radical, e.g. methyl, ethyl, propyl, butyl, hexyl, 2-ethylhexyl, stearyl, lauryl, cyclohexyl, benzyl, trifluoromethyl, hexafluoropropyl or tetrafluoropropyl (meth)acrylate, polypropylene glycol mono(meth)acrylates, polyethylene glycol mono(meth)acrylates, poly(meth)acrylates of polyhydric alcohols, e.g. glycerol di(meth)acrylate, trimethylolpropane di(meth)acrylate, pentaerythritol di- or tri(meth)acrylate, diethylene glycol bis(mono)-2-acryloxy)ethyl) carbonate, poly(meth)acrylates of alcohols which in turn themselves have a free-radically polymerizable group, e.g. esters of (meth)acrylic acid and vinyl and/or allyl alcohol;

vinyl esters of other aliphatic or aromatic carboxylic acids, e.g. vinyl acetate, vinyl propionate, vinyl butanoate, vinyl hexanoate, vinyl octanoate, vinyl decanoate, vinyl stearate, vinyl palmitate, vinyl crotonate, divinyl adipate, divinyl sebacate, 2-vinyl 2-ethylhexanoate, vinyl trifluoroacetate;

allyl esters of other aliphatic or aromatic carboxylic acids, e.g. allyl acetate, allyl propionate, allyl butanoate, allyl hexanoate, allyl octanoate, allyl decanoate, allyl stearate, allyl palmitate, allyl crotonate, allyl salicylate, allyl lactate, diallyl oxalate, allyl stearate, allyl succinate, diallyl glutarate, diallyl adipate, diallyl pimelate, diallyl cinnamate, diallyl maleate, diallyl phthalate, diallyl isophthalate, triallyl benzene-1,3,5-tricarboxylate, allyl fluoroacetate, allyl perfluorobutyrate, allyl perfluorooctanoate;

β,γ-unsaturated carboxylic acids and derivatives thereof, e.g. vinylacetic acid, 2-methylvinylacetic acid, isobutyl 3-butenoate, allyl 3-butenoate, allyl 2-hydroxy-3-butenoate, diketene;

Particularly suitable sulfonic acids are, for example, vinylsulfonic acid, allylsulfonic acid and methallylsulfonic acid, and also their esters and halides, vinyl benzenesulfonate, 4-vinylbenzenesulfonamide.

It is also possible to use mixtures of two or more of the above-described carboxylic and/or sulfonic acids.

The polymer IIb1 can be obtained by reaction of from 5 to 100% by weight, preferably from 30 to 70% by weight, based on the polymer IIb1, of the above-defined condensation product and from 0 to 95% by weight, in particular from 30 to 70% by weight, based on the polymer IIb1, of a compound (c).

2) Homopolymers, copolymers or block copolymers IIb2 (polymers IIb2), obtainable by polymerization of b1) from 5 to 75% by weight, based on the polymer IIb2, of a polymerizable compound (d), preferably an unsaturated compound (d) capable of free-radical polymerization, which is different from the abovementioned carboxylic acid or sulfonic acid (b) or a derivative thereof, or a mixture of two or more thereof, and b2) from 25 to 95% by weight, based on the polymer IIb2, of the further compound (c) having a mean molecular weight (number average) of at least 5000 and polyether segments in a main or side chain.

Specific examples of compounds (d) which are capable of free-radical polymerization and can be used for preparing the polymer Ib2 are:

Olefinic hydrocarbons such as ethylene, propylene, butylene, isobutene, hexene or higher homologues and vinylcyclohexane; (meth)acrylonitrile;

halogen-containing olefinic compounds such as vinylidene fluoride, vinylidene chloride, vinyl fluoride, vinyl chloride, hexafluoropropene, trifluoropropene, 1,2-dichloroethylene, 1,2-difluoroethylene and tetrafluoroethylene;

vinyl alcohol, vinyl acetate, N-vinylpyrrolidone, N-vinylimidazole, vinylformamide;

phosphonitrilic chlorides such as phosphonitrilic dichloride, hexachloro(triphosphazene), and also their derivatives which are partially or fully substituted by alkoxy, phenoxy, amino and fluoroalkoxy groups, i.e. compounds which can be polymerized to form polyphosphazenes;

aromatic, olefinic compounds such as styrene, α-methylstyrene;

vinyl ethers such as methyl vinyl ether, ethyl vinyl ether, propyl vinyl ether, isopropyl vinyl ether, butyl vinyl ether, isobutyl vinyl ether, hexyl vinyl ether, octyl vinyl ether, decyl vinyl ether, dodecyl vinyl ether, 2-ethylhexyl vinyl ether, cyclohexyl vinyl ether, benzyl vinyl ether, trifluoromethyl vinyl ether, hexafluoropropyl vinyl ether or tetrafluoropropyl vinyl ether.

It is, of course, also possible to use mixtures of the abovementioned compounds (d), which then gives copolymers which, depending on the method of preparation, have the monomers randomly distributed or arranged in blocks (block copolymers).

These compounds (d) are, like the above-described condensation products, polymerized in conventional ways that are well known to those skilled in the art, preferably polymerized by a free-radical mechanism; as regards the molecular weights obtained, what is said below with regard to the compound (c) applies.

Possible compounds (c) are first and foremost compounds having a mean molecular weight (number average) of at least 5000, preferably from 5000 to 20,000,000, in particular from 100,000 to 6,000,000, which are able to solvate lithium cations and function as binders.

Suitable compounds (c) are, for example, polyethers and copolymers comprising at least 30% by weight of the following structural unit, based on the total weight of the compound (c):

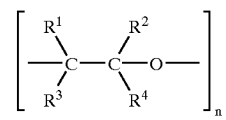

where $R^1$, $R^2$, $R^3$ and $R^4$ are aryl groups, alkyl groups, preferably methyl groups, or hydrogen, are identical or different and may contain heteroatoms such as oxygen, nitrogen, sulfur or silicon.

Such compounds are described, for example, in: M. B. Armand et. al., Fast Ion Transport in Solids, Elsevier, New York, 1979, pp. 131–136, or in FR-A 7832976.

The compound (c) can also be a mixture of such compounds.

The polymer IIb2 can be obtained by reaction of from 5 to 75% by weight, preferably from 30 to 70% by weight, based on the polymer IIb2, of a compound (d) and from 25 to 95% by weight, in particular from 30 to 70% by weight, based on the polymer IIb2, of a compound (c).

3) Polycarbonates such as polyethylene carbonate, polypropylene carbonate, polybutadiene carbonate, polyvinylidene carbonate.

4) Homopolymers, copolymers and block copolymers prepared from a) olefinic hydrocarbons such as ethylene, propylene, butylene, isobutene, propene, hexene or higher homologues, butadiene, cyclopentene, cyclohexene, norbornene, vinylcyclohexane, 1,3-pentadiene, 1,3-, 1,4- and 1,5-hexadiene, isoprene, vinylnorbornene;

b) aromatic hydrocarbons such as styrene and methylstyrene;

c) acrylic or methacrylic esters such as methyl, ethyl, propyl, isopropyl, butyl, isobutyl, hexyl, octyl, decyl, dodecyl, 2-ethylhexyl, cyclohexyl, benzyl, trifluoromethyl, hexafluoropropyl or tetrafluoropropyl acrylate or methacrylate;

d) acrylonitrile, methacrylonitrile, N-methylpyrrolidone, N-vinylimidazole, vinyl acetate;

e) vinyl ethers such as methyl vinyl ether, ethyl vinyl ether, propyl vinyl ether, isopropyl vinyl ether, butyl vinyl ether, isobutyl vinyl ether, hexyl vinyl ether, octyl vinyl ether, decyl vinyl ether, dodecyl vinyl ether, 2-ethylhexyl vinyl ether, cyclohexyl vinyl ether, benzyl vinyl ether, trifluoromethyl vinyl ether, hexafluoropropyl vinyl ether, tetrafluoropropyl vinyl ether;

f) polymers and copolymers of halogen-containing olefinic compounds such as vinylidene fluoride, vinylidene chloride, vinyl fluoride, vinyl chloride, hexafluoropropene, trifluoropropene, 1,2-dichloroethylene, 1,2-difluoroethylene and tetrafluoroethylene; preferably polymers or copolymers of vinyl chloride, acrylonitrile, vinylidene fluoride; copolymers of vinyl chloride and vinylidene chloride, vinyl chloride and acrylonitrile, vinylidene fluoride and hexafluoropropylene, vinylidene fluoride and hexafluoropropylene; terpolymers of vinylidene fluoride and hexafluoropropylene together with a member of the group consisting of vinyl fluoride, tetrafluoroethylene and a trifluoroethylene; in particular a copolymer of vinylidene fluoride and hexafluoropropylene; and more preferably a copolymer comprising from 75 to 92% by weight of vinylidene fluoride and from 8 to 25% by weight of hexafluoropropylene;

g) 2-vinylpyridine, 4-vinylpyridine, vinylene carbonate.

In the preparation of the abovementioned polymers, regulators such as mercaptans can be used if necessary and/or desired.

5) Polyurethanes, for example those obtainable by reaction of
   a) organic diisocyanates having from 6 to 30 carbon atoms, e.g. aliphatic, noncyclic diisocyanates such as hexamethylene 1,5-diisocyanate and hexamethylene 1,6-diisocyanate, cyclic aliphatic diisocyanates such as cyclohexylene 1,4-diisocyanate, dicyclohexylmethane diisocyanate and isophorone diisocyanate or aromatic diisocyanates such as tolylene 2,4-diisocyanate, tolylene 2,6-diisocyanate, m-tetramethylxylene diisocyanate, p-tetramethylxylene diisocyanate, tetrahydronaphthylene 1,5-diisocyanate and diphenylmethane 4,4'-diisocyanate or mixtures of such compounds, with
   b) polyhydric alcohols such as polyesterols, polyetherols and diols.

The polyesterols are advantageously predominantly linear polymers having terminal OH groups, preferably ones having two or three, in particular two, OH end groups. The acid number of the polyesterols is less than 10 and preferably less than 3. The polyesterols can be prepared in a simple manner by esterification of aliphatic or aromatic dicarboxylic acids having from 4 to 15 carbon atoms, preferably from 4 to 6 carbon atoms, with glycols, preferably glycols having from 2 to 25 carbon atoms, or by polymerization of lactones having from 3 to 20 carbon atoms. Dicarboxylic acids which can be used are, for example, glutaric acid, pimelic acid, suberic acid, sebacic acid, dodecanoic acid and preferably adipic acid and succinic acid. Suitable aromatic dicarboxylic acids are terephthalic acid, isophthalic acid, phthalic acid or mixtures of these dicarboxylic acids with other dicarboxylic acids, e.g. diphenic acid, sebacic acid, succinic acid and adipic acid. The dicarboxylic acids can be used individually or as mixtures. To prepare the polyesterols, it may be advantageous to use the corresponding acid derivatives such as carboxylic anhydrides or carboxalic acid chlorides in place of the dicarboxylic acids. Examples of suitable glycols are diethylene glycol, 1,5-pentanediol, 1,10-decanediol and 2,2,4-trimethylpentane-1,5-diol. Preference is given to using 1,2-ethanediol, 1,3-propanediol, 2-methyl-1,3-propanediol, 1,4-butanediol, 1,6-hexanediol, 2,2-dimethylpropane-1,3-diol, 1,4-dimethylolcyclo-hexane, 1,4-diethanolcyclohexane and ethoxylated or propoxylated products of 2,2-bis(4-hydroxyphenyl)-propane (bisphenol A). Depending on the desired properties of the polyurethanes, the polyols can be used alone or as mixtures in various mixing ratios. Suitable lactones for preparing the polyesterols are, for example, α,α-dimethyl-β-propiolactone, γ-butyrolactone and preferably α-caprolactone.

The polyetherols are essentially linear substances having terminal hydroxyl groups and containing ether bonds. Suitable polyetherols can easily be prepared by polymerization of cyclic ethers such as tetrahydrofuran or by reaction of one or more alkylene oxides having from 2 to 4 carbon atoms in the alkylene radical with an initiator molecule containing two active hydrogen atoms in bound form in the alkylene radical. Examples of suitable alkylene oxides are ethylene oxide, 1,2-propylene oxide, epichlorohydrin, 1,2-butylene oxide and 2,3-butylene oxide. The alkylene oxides can be used individually, alternately in succession or as a mixture. Examples of suitable initiator molecules are water, glycols such as ethylene glycol, propylene glycol, 1,4-butanediol and 1,6-hexanediol, amines such as ethylenediamine, hexamethylenediamine and 4,4'-diaminodiphenylmethane and aminoalcohols such as ethanolamine. Suitable polyesterols and polyetherols and also their preparation are described, for example, in EP-B 416 386, while suitable polycarbonate diols, preferably those based on 1,6-hexanediol, and their preparation are described, for example, in U.S. Pat. No. 4,131,731.

It can be advantageous to use amounts of up to 30% by weight, based on the total mass of the alcohols, of aliphatic diols having from 2 to 20, preferably from 2 to 10, carbon atoms, e.g. 1,2-ethanediol, 1,3-propanediol, 1,4-butanediol, 1,6-hexanediol, 1,5-pentanediol, 1,10-decanediol, 2-methyl-1,3-propanediol, 2,2-dimethyl-1,3-propanediol, 2-methyl-2-butyl-1,3-propanediol, 2,2-dimethyl-1,4-butanediol, 1,4-dimethylolcyclohexane, neopentyl glycol hydroxypivalate, diethylene glycol, triethylene glycol and methyldiethanolamine, or aromatic-aliphatic or aromatic-cycloaliphatic diols having from 8 to 30 carbon atoms, where possible aromatic structures are heterocyclic ring systems or preferably isocyclic ring systems such as naphthalene or, in particular, benzene derivatives such as bisphenol A, symmetrically diethoxylated bisphenol A, symmetrically dipropoxylated bisphenol A, more highly ethoxylated or propoxylated bisphenol A derivatives or bisphenol F derivatives, and also mixtures of such compounds.

It can be advantageous to use amounts of up to 5% by weight, based on the total mass of the alcohols, of aliphatic triols having from 3 to 15, preferably from 3 to 10, carbon atoms, e.g. trimethylolpropane or glycerol, the reaction product of such compounds with ethylene oxide and/or propylene oxide and also mixtures of such compounds.

The polyhydric alcohols may bear functional groups, for example neutral groups such as siloxane groups, basic groups such as, in particular, tertiary amino groups or acidic groups or their salts or groups which are easily transformed into acidic groups, which are introduced via a polyhydric alcohol. Preference is given to using diol components which bear such groups, e.g. N-methyldiethanolamine, diethyl N,N-bis(hydroxyethyl)aminomethylphosphonate or 3-sulfopropyl N,N-bis-(hydroxyethyl)-2-aminoacetate, or dicarboxylic acids which bear such groups and can be used for the preparation of polyesterols, e.g. 5-sulfoisophthalic acid.

Acidic groups are, in particular, the phosphoric acid, phosphonic acid, sulfuric acid, sulfonic acid, carboxyl or ammonium groups.

Groups which are easily transformed into acidic groups are, for example, the ester group or salts, preferably of alkali metals such as lithium, sodium or potassium.

6) The above-described polyesterols themselves, where attention has to be paid to obtaining molecular weights in the range from 10,000 to 2,000,000, preferably from 50,000 to 1,000,000.

7) Polyamines, polysiloxanes and polyphosphazenes, in particular those which have already been discussed in the description of the polymer IIb2.

8) Polyetherols as have been described, for example, in the above discussion of the polymer IIb1 as compound (c) or in the discussion of the polyurethanes.

It is of course also possible to use mixtures of the abovementioned polymers IIb. The copolymers IIb used according to the present invention can, depending on the method of preparation, have the monomers distributed randomly or arranged in blocks (block copolymers).

The polymers Ia and IIb are polymerized by conventional methods which are well known to those skilled in the art, preferably polymerized by a free-radical mechanism. The polymers Ia and IIb can be used either in high molecular weight or oligomeric form or as mixtures thereof.

The proportion of polymer Ia in the polymeric binder II is generally from 1 to 100% by weight, preferably from 20 to 80% by weight, more preferably from 30 to 60% by weight. Correspondingly, the proportion of the polymer IIb in the polymeric binder II is generally from 0 to 99% by weight, preferably from 20 to 80% by weight and more preferably from 40 to 70% by weight.

The present invention preferably provides the following compositions:

Compositions as defined above in which the polymer IIa has, as part of the chain, at the end(s) of the chain and/or laterally on the chain, at least one reactive group RGa which in the triplet excited state under the action of heat and/or UV radiation is capable of hydrogen abstraction and has, as part of the chain, at the end(s) of the chain and/or laterally on the chain, at least one group RGb which is different from RGa and is coreactive with RGa, with at least one group RGa and at least one group RGb being present on average over all polymer molecules.

Compositions as defined above in which the polymer IIa is a polymer or copolymer of an acrylate or methacrylate and has reactive groups RGa which comprise benzophenone units and reactive groups RGb which comprise dihydrodicyclopentadiene units.

Compositions as defined above in which the polymer IIb is selected from the group consisting of a polymer or copolymer of vinyl chloride, acrylonitrile, vinylidene fluoride; a copolymer of vinyl chloride and vinylidene chloride, vinyl chloride and acrylonitrile, vinylidene fluoride and hexafluoropropylene, vinylidene fluoride and hexafluoropropylene; a terpolymer of vinylidene fluoride and hexafluoropropylene together with a member of the group consisting of vinyl fluoride, tetrafluoroethylene and a trifluoroethylene.

Compositions as defined above in which the polymer Ia is a polymer or copolymer of an acrylate or methacrylate and has reactive groups RGa comprising benzophenone units and reactive groups RGb comprising dihydrodicyclopentadiene units and the polymer IIb is a copolymer of vinylidene fluoride and hexafluoropropylene.

The compositions of the present invention may further comprise a plasticizer III. However, it is not necessary for a plasticizer to be present.

If present, the proportion of plasticizer III, based on the composition, is from 0.1 to 100% by weight, preferably from 0.5 to 50% by weight and in particular from 1 to 20% by weight.

Plasticizers III which can be used are aprotic solvents, preferably those which solvate Li ions, e.g. dimethyl carbonate, ethyl methyl carbonate, diethyl carbonate, dipropyl carbonate, diisopropyl carbonate, dibutyl carbonate, propylene carbonate; cyclic carbonates of the empirical formula $C_nH_{n+1}O_y$, n=2–30, m=3–7, e.g. ethylene carbonate, 1,2-propylene carbonate, 1,3-propylene carbonate, 1,2-butylene carbonate, 1,3-butylene carbonate, 1,4-butylene carbonate, 2,3-butylene carbonate; oligoalkylene oxides, such as dibutyl ether, di-tert-butyl ether, dipentyl ether, dihexyl ether, diheptyl ether, dioctyl ether, dinonyl ether, didecyl ether, didodecyl ether, ethylene glycol dimethyl ether, ethylene glycol diethyl ether, 1-tert-butoxy-2-methoxyethane, 1-tert-butoxy-2-ethoxyethane, 1,2-dimethoxypropane, 2-methoxyethyl ether, 2-ethoxyethyl ether, diethylene glycol dibutyl ether, dimethylene glycol tert-butyl methyl ether, triethylene glycol dimethyl ether, tetraethylene glycol dimethyl ether, γ-butyrolactone, dimethylformamide; dimethyl-γ-butyrolactone, diethyl-γ-butyrolactone, γ-valerolactone, 4,5-dimethyl-1,3-dioxolan-2-one, 4,4-dimethyl-1,3-dioxolan-2-one, 4-ethyl-1,3-dioxolan-2-one, 4-methyl-5-ethyl-1,3-dioxolan-2-one, 4,5-diethyl-1,3-dioxolan-2-one, 4,4-diethyl-1,3-dioxolan-2-one, 1,3-dioxan-2-one, 4-methyl-1,3-dioxan-2-one, 5-methyl-1,3-dioxan-2-one, 4,4-dimethyl-1,3-dioxan-2-one, 5,5-dimethyl-1,3-dioxan-2-one, 4,6-dimethyl-1,3-dioxan-2-one, 4,4,6-trimethy-1,3-dioxan-2-one, 5,5-diethyl-1,3-dioxan-2-one, spiro-(1,3-oxa-2-cyclohexanon)-5',5', 5',3'-oxacyclohexane; 4-dimethyl-ethoxysilyl-1,2-butylene carbonate; dicarboxylic esters of the formula $R^1OCOOR^2OCOOR^3$ ($R^1$, $R^2$, $R^3$ $C_1$–$C_{20}$-hydrocarbons), organic esters of the formula $R^1$—$COOR^2$ ($R^1$ and $R^2$=$C_1$–$C_{20}$-hydrocarbons); hydrocarbons of the formula $C_nH_{2n+2}$ where 7<n<50; organic phosphorus compounds, in particular phosphates and phosphonates, e.g. trimethyl phosphate, triethyl phosphate, tripropyl phosphate, tributyl phosphate, triisobutyl phosphate, tripentyl phosphate, trihexyl phosphate, trioctyl phosphate, tris(2-ethylhexyl) phosphate, tridecyl phosphate, diethyl n-butyl phosphate, tris(butoxyethyl) phosphate, tris(2-methoxyethyl) phosphate, tris(tetrahydrofuryl) phosphate, tris(1H, 1H,5H-octafluoropentyl) phosphate, tris(1H, 1H-trifluoroethyl) phosphate, tris(2-(diethylamino)ethyl) phosphate, tris(methoxyethoxyethyl) phosphate, tris(methoxyethoxy)trifluorophosphazene, tris(ethoxycarbonyloxyethyl) phosphate, diethyl ethylphosphonate, dipropyl propylphosphonate, dibutyl butylphosphonate, dihexyl hexylphosphonate, dioctyl octylphosphonate, ethyl dimethylphosphonoacetate, methyl diethylphosphonoacetate, triethyl phosphonoacetate, dimethyl (2-oxopropyl)phosphonate, diethyl (2-oxopropyl)phosphonate, dipropyl (2-oxopropyl)phosphonate, ethyl diethoxyphosphinylformate, trimethylphosphonoacetate, triethylphosphonoacetate, tripropyl phosphonoacetate, tributyl phosphonoacetate; organic sulfur compounds such as sulfates, sulfonates, sulfoxides, sulfones and sulfites, e.g. dimethyl sulfite, diethyl sulfite, glycol sulfite, dimethyl sulfone, diethyl sulfone, diethylpropyl sulfone, dibutyl sulfone, tetramethylene sulfone, methylsulfolane, dimethyl sulfoxide, diethyl sulfoxide, dipropyl sulfoxide, dibutyl sulfoxide, tetramethylene sulfoxide, ethyl methanesulfonate, 1,4-butanediol bis(methanesulfonate), diethyl sulfate, dipropyl sulfate, dibutyl sulfate, dihexyl sulfate, dioctyl sulfate, $SO_2ClF$; nitriles such as acrylonitrile;

dispersants, in particular those having a surfactant structure; and also mixtures thereof.

In addition, it is possible to use, quite generally, suitable organic compounds such as alkanes $C_nH_xF_y$ where n=5–30, x+y=2n+2; ethers $C_nH_xF_yO_z$ where n=5–30, x+y=2n+2, z=1–14; ketones $C_nH_xF_yO_3$ where n=5–30, x+y=2n; esters $C_nH_xF_yO_2$ where n=5–30, x+y=2n; carbonates $C_nH_xF_yO_3$ where n=5–30, x+y=2n; lactones $C_nH_xF_yO_2$ where n=5–20, x+y=2n–2; cyclic carbonates $C_nH_xF_yO_3$ where n=5–20, x+y=2n–2; and esters of boric acid where
R—$R^4$=$C_1$–$C_{10}$-hydrocarbons and
X=C-Clo-hydrocarbons, $Si(CH_3)_2$
m=1 or 2

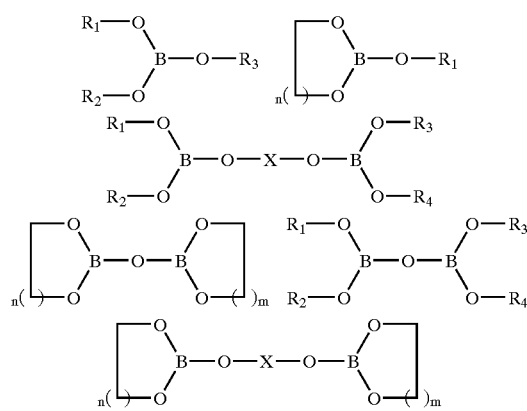

in particular trimethyl borate, triethyl borate, tripropyl borate, tributyl borate, trimethylene borate, 2-methyl-1,3,2-dioxaborinane, 2-ethyl-1,3,2-dioxaborinane, 2-propyl-1,3,2-dioxaborinane, 2-butyl-1,3,2-dioxaborinane, 2-phenyl-1,3,2-dioxaborinane, as plasticizers V.

Furthermore, at least one ester of the formulae (E1) to (E5), as shown below, can be used as plasticizer (V):

 (E1)

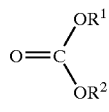 (E2)

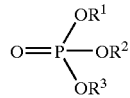 (E3)

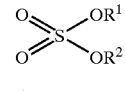 (E4)

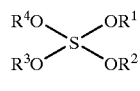 (E5)

where $R^1$, $R^2$, $R^3$, $R^4$ are identical or different and are each, independently of one another, a linear or branched $C_1$–$C_4$-alkyl group, $(-CH_2-CH_2-O)_n-CH_3$ where n=1–3, a $C_3$–$C_6$-cycloalkyl group, an aromatic hydrocarbon group which may in turn be substituted, with the proviso that at least one of the groups $R^1$, $R^2$, $R^3$ and $R^4$ is $(-CH_2-CH_2-O)_n-CH_3$ where n=1–3.

Among the abovementioned esters of the formulae (E1) to (E5), preference is given to using the phosphoric esters of the formula (E3).

Examples of groups $R^1$, $R^2$ and, if present, $R^3$ and/or $R^4$ are the methyl, ethyl, nand iso-propyl, n- and tert-butyl, cyclopentyl and cyclohexyl groups and the benzyl group and also $(-CH_2-CH_2-O)_n-CH_3$ where n=1–3, but, as already mentioned above, at least one of the groups $R^1$, $R^2$, $R^3$ and $R^4$ has to be $(CH_2-CH_2-O)_n-CH_3$ in which n=1–3, preferably 1 or 2.

Further preference is given to using esters of the formulae (E1) to (E5) in which $R^1$, $R^2$ and, if present, $R^3$ and/or $R^4$ are identical and are each $-CH_2-CH_2O-CH_3$ or $(-CH_2-CH_2-O)_2-CH_3$, with the corresponding phosphoric esters again being preferred.

Examples of compounds which are particularly preferably used are the compounds of the formulae (E1a) to (E5a):

 (E1a)

 (E2a)

 (E3a)

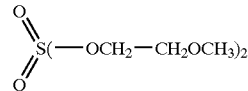 (E4a)

and

 (E5a)

The esters described here have properties which make them particularly useful as plasticizers in the films and generally have a viscosity at room temperature of <10 mPas, preferably <5 mPas and in particular <3 mPas. They have boiling points of generally about 200° C. or above, preferably about 250° C. or above and in particular about 300° C. or above, in each case measured at atmospheric pressure, and at the temperatures of from about −50° C. to about 150° C. which occur during use have a sufficiently low vapor pressure of from about $10^{-5}$ to about 100. Owing to their boiling points, they can be distilled and can thus be prepared in high purity. Furthermore, these esters are liquid over a wide temperature range at atmospheric pressure; they are generally still liquid down to about −30° C., preferably down to about −40° C. The esters described here can be used as solvents in electrolyte systems for Li-ion accumulators at at least about 80° C., preferably at least about 120° C., more preferably at least about 150° C.

Of course, the esters used according to the present invention can also be employed as mixtures with the abovementioned plasticizers.

Preference is given to solvent combintions which have a sufficiently low viscosity and are able to solvate the ions of the electrolyte salts strongly, are liquid over a wide temperature range and are sufficiently electrochemically and chemically stable and hydrolysis resistant.

The esters used according to the present invention are prepared by conventional methods as are described, for example, in K. Mura Kami in Chem. High Polymers (Japan), 7, pp. 188–193 (1950) and in H. Steinberg Organoboron Chemistry, chapter 5, J. Wiley&Sons, N.Y. 1964. These methods generally start out from the parent acids, acid anhydrides or chlorides of the esters, e.g. boric acid, $C(O)Cl_2$, $POCl_3$, $SO_2Cl_2$ and $SiCl_4$, which are reacted in a known manner with the appropriate monohydric or polyhydric alcohols or etherols.

The compositions of the present invention can be dissolved or dispersed in an inorganic or organic liquid diluent, preferably an organic liquid diluent, where the mixture according to the present invention should have a viscosity of preferably from 100 to 50,000 mPas, and subsequently applied to a support material in a manner known per se, for example by spray coating, casting, dipping, spin coating, roller coating, printing by letterpress, gravure or flatbed processes or screen printing. Further processing can be carried out in a customary way, e.g. by removing the diluent and curing the mixture.

Suitable organic diluents are aliphatic ethers, in particular tetrahydrofuran and dioxane, hydrocarbons, in particular hydrocarbon mixtures such as petroleum spirit, toluene and xylene, aliphatic esters, in particular ethyl acetate and butyl acetate, and ketones, in particular acetone, ethyl methyl ketone and cyclohexanone, and also DMF and NMP. It is also possible to use combinations of such diluents.

Suitable support materials are the materials customarily used for electrodes, preferably metals such as aluminum and copper. It is likewise possible to use temporary intermediate supports such as films, in particular polyester films such as polyethylene terephthalate films. Such films can advantageously be provided with a release layer, preferably of polysiloxanes.

The production of these solid electrolytes and separators can likewise be carried out by thermoplastic processing, for example by injection molding, melt casting, pressing, kneading or extrusion of the mixture according to the present invention, if desired followed by a calendering step.

After formation of the film of the mixture according to the invention, volatile components such as solvents or plasticizers can be removed.

The crosslinking of the composition of the present invention can be carried out in a manner known per se, for example by irradiation with ionic or ionizing radiation, an electron beam, preferably at an accelerator voltage of from 20 to 2000 kV and a radiation dose of from 5 to 50 Mrad, UV or visible light, where an initiator such as benzil dimethyl ketal or 1,3,5-trimethylbenzoyl triphenylphosphine oxide can be added in amounts of, in particular, not more than 1% by weight based on the polymer IIa and crosslinking can be carried out over a period of generally from 0.5 to 15 minutes; the addition of an initiator is not necessary since the herein used systems are generally self-crosslinking by thermal crosslinking via free-radical polymerization, preferably at above 60° C., where an initiator such as azobisisobutyronitrile can be advantageously added in amounts of generally not more than 5% by weight, preferably from 0.05 to 1% by weight, based on the polymer IIa; by electrochemically induced polymerization; or by ionic polymerization, for example by acid-catalyzed cationic polymerization, where possible catalysts are first and foremost acids, preferably Lewis acids such as $BF_3$ or, in particular, $LiBF_4$ or $LiPF_6$. Catalysts comprising lithium ions, e.g. $LiBF_4$ or $LiPF_6$, can advantageously remain as electrolyte salt in the solid electrolyte or separator.

The above-described crosslinking can be, but does not necessarily have to be, carried out under inert gas.

If the composition of the present invention is to be used as solid electrolyte or separator in an electrochemical cell, a dissociable compound comprising lithium cations, viz. an electrolyte salt, and, if desired, further additives such as, in particular, organic solvents, viz. an electrolyte, are incorporated.

Some or all of these materials can be mixed in during production of the layer of the composition or can be introduced into the layer after it has been produced.

Electrolyte salts which can be used are those which are generally known and described, for example, in EP-A 0 096 629. According to the present invention, preferred electrolyte salts are $LiPF_6$, $LiBF_4$, $LiClO_4$, $LiAsF_6$, $LiCF_3SO_3$, $LiC(CF_3SO_2)_3$, $LiN(CF_3SO_2)_2$, $LiN(SO_2C_nF_{2n+1})_2$, $LiC[(C_nF_{2n+1})SO_2]_3$, $Li(C_nF_{2n+1})SO_2$, where n is in each case from 2 to 20, $LiN(SO_2F)_2$, $LiAlCl_4$, $LiSiF_6$, $LiSbF_6$, $(RSO_2)_n XLi$ ($_nX=10$, $_1S$, $_2N$, $_2P$, $_3C$, $_3Si$; $R=C_mF_2$ m+1 where m=0–10 or $C_1$–$C_{20}$-hydrocarbons), Li-imid salts or a mixture of two or more thereof; particular preference is given to using $LiPF_6$ as electrolyte salt.

Suitable organic electrolytes are the compounds discussed above under "plasticizers", with preference being given to using the customary organic electrolytes, preferably esters such as ethylene carbonate, propylene carbonate, dimethyl carbonate and diethyl carbonate or mixtures of such compounds.

Solid electrolytes, separators and/or electrodes according to the present invention which are suitable for electrochemical cells advantageously have a thickness of from 5 to 500 $\mu$m, preferably from 10 to 500 $\mu$m, more preferably from 10 to 200 $\mu$m and in particular from 20 to 100 $\mu$m.

The compositions of the present invention can be used in electrochemical cells as sole solid electrolyte and/or separator and/or electrode or in admixture with other solid electrolytes, separators and/or electrodes. They are preferably used as solid electrolyte.

The present invention also provides a composite which can be used, in particular, in electrochemical cells, preferably in the form of a film, more preferably in the form of a film having a total thickness of from 15 to 1500 $\mu$m, in particular having a total thickness of from 50 to 500 $\mu$m, comprising at least one first layer which comprises an above-defined composition comprising a compound Ib or a compound Ic and at least one second layer which comprises an above-defined composition which comprises a solid Ia and is free of compounds Ic and Ib. This composite can also be combined with conventional electrodes, e.g. a graphite anode. The above-defined first layer then comprises a compound Ib so that the following element is formed:

anode (conventional) / second layer  / first layer
                         (separator)   (cathode)

In addition, the present invention provides a process for producing such a composite, which comprises the following steps:

(I) production of at least one first layer, as defined above;
(II) production of at least one second layer, as defined above; and
(III) subsequent bringing together of the first layer or layers and the second layer or layers by a conventional coating process.

The second layer or layers is/are preferably produced on a temporary support. According to the present invention, it is here possible to use customarily employed temporary supports, e.g. a release film of a polymer or of a preferably coated paper, for example a siliconized polyester film. However, this second layer can also be produced on a permanent support such as a contact electrode or without any support at all.

The bringing together or the production of the above-defined layers is carried out by pressureless methods for coating or for the production of films, e.g. casting or doctor blade coating, or by processing methods which employ pressure, e.g. extrusion, laminating, calendering or pressing. Due to the self-crosslinkability of the polymers IIa as used according to the invention a step wherein the system is crosslinked after bringing together, e.g. by heat laminating said layers is not necessary. In case it is desired to crosslink the system after heat lamination, the composite produced in this way can be crosslinked or cured thermally, electrochemically or by means of radiation.

As can be seen from the above, it is thus readily possible to produce a composite comprising release film/separator (second layer)/electrode (first layer).

Furthermore, double-sided coating makes it possible to provide a composite comprising anode/separator/cathode.

This can be achieved, for example, by the following procedure:

Firstly, a first compound Ic, e.g. graphite or conductive carbon black, a polymeric binder II, an electrolyte salt and a plasticizer, e.g. propylene carbonate, are mixed with one another and the resulting mixture is cast onto a contact electrode and subsequently irradiated with UV light (component 1). Subsequently, a cathode material, e.g. $LiMn_2O_4$, is applied to a contact electrode coated with conductive carbon black, and a mixture of the composition of the present invention which comprises a solid Ia and is free of compounds Ib and Ic, an electrolyte salt and a plasticizer is then cast onto this cathode material. This composite too is subsequently irradiated with UV light (component 2). Bringing together the two above-described components gives a composite which can, in combination with any solid and/or liquid electrolyte, be used as an electrochemical cell.

A solid electrolyte/anode or solid electrolyte/cathode composite or a cathode/solid electrolyte/anode composite can be produced without further additives by laminating together the separator film and the anode film and/or cathode film at >80° C. It is thus readily possible to laminate, for example, a composition according to the present invention comprising a solid Ia onto a conventional anode or cathode to give an anode or cathode/solid electrolyte (separator) composite which can in turn be combined with a conventional cathode or anode.

An anode/separator/cathode composite as described above can also be produced without use of a support or the contact electrodes, since the composite consisting of a first layer and a second layer, as defined above, has sufficient intrinsic mechanical stability for use in electrochemical cells.

The composition of the present invention thus makes the following configurations possible.

| Cathode | Solid electrolyte/separator | Anode |
|---|---|---|
| conventional | composition of the present invention | conventional |
| composition of the present invention | composition of the present invention | composition of the present invention |
| composition of the present invention | composition of the present invention | conventional |
| conventional | composition of the present invention | composition of the present invention |
| conventional | conventional | composition of the present invention |
| composition of the present invention | conventional | conventional |

The charging of such composites with an electrolyte and an electrolyte salt can be carried out either before or preferably after the bringing together of the layers, if applicable after combination with suitable contact electrodes, e.g. a metal foil, and even after introduction of the composite into a battery housing. The specific microporous structure of the layers when the mixture of the present invention is used, in particular because of the presence of the above-defined solid in the separator and possibly in the electrodes, makes it possible for the electrolyte and the electrolyte salt to be drawn into the pores and the air to be displaced. Charging with the electrolyte and the electrolyte salt can be carried out at temperatures in the range from 0° C. to about 100° C., depending on the electrolyte used.

The electrochemical cells of the present invention can be used, in particular, as board, automobile, instrument or planar battery, as well as a battery for static applications and a battery electrotraction.

As can be seen from the above, the present invention also provides for the use of the composition of the present invention or the above-described composite for producing a solid electrolyte, a separator or an electrode or in a sensor, an electrochromic window, a display, a capacitor or an ion-conducting film, and also provides a solid electrolyte, a separator, an electrode, a sensor, an electrochromic window, a display, a capacitor or an ion-conducting film which each comprise the mixture of the invention or the above-described composite.

Furthermore, it provides an electrochemical cell comprising a solid electrolyte, separator or an electrode as defined above or a combination of two or more thereof, and provides for the use of the above-defined electrochemical cell as an automobile battery, instrument battery or planar battery.

The composition of the present invention has the following advantages over the Systems hitherto provided for use in electrochemical cells:

- The photocrosslinking step, in the production of the cast film, if carried out at all, does not require inert gas conditions;
- the mechanical properties of the films resulting from the composition can be controlled via the composition of the polymer IIa to give films ranging from hard/brittle to flexible/elastic;
- as a result of the presence of the polymer IIb, the resulting film is thermoplastic and can be laminated thermally onto the active electrodes without addition of further auxiliaries.

The present invention additionally provides for the use of a polymer Ia, as defined above, as crosslinker system in a solid electrolyte, a separator or an electrode.

The present invention is illustrated by the examples below.

Figure 2:
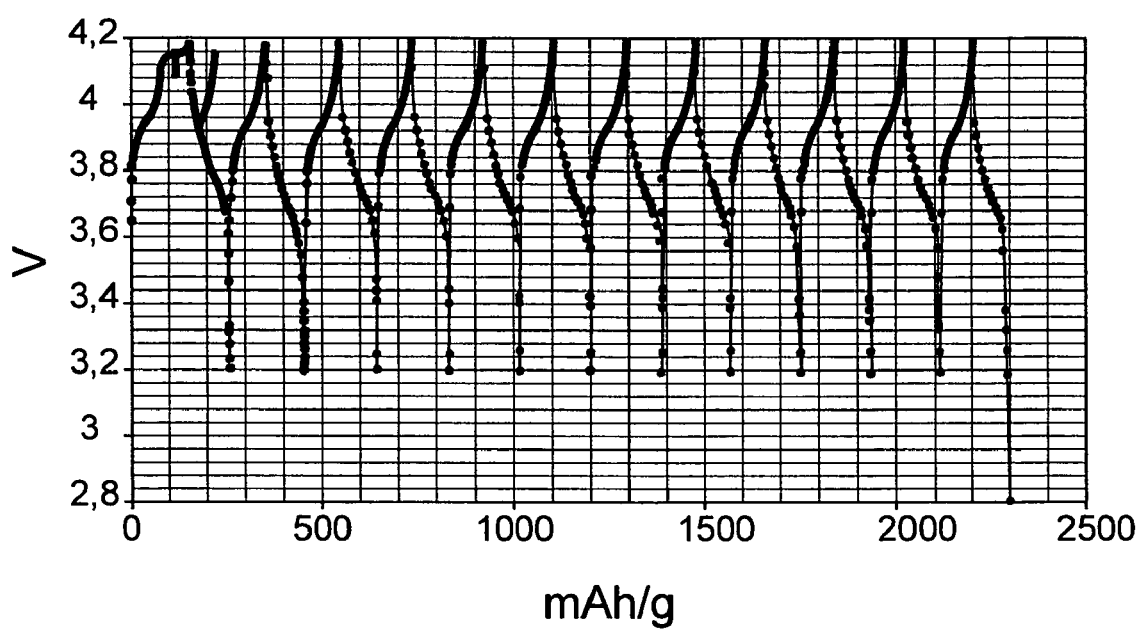
Figure 3:
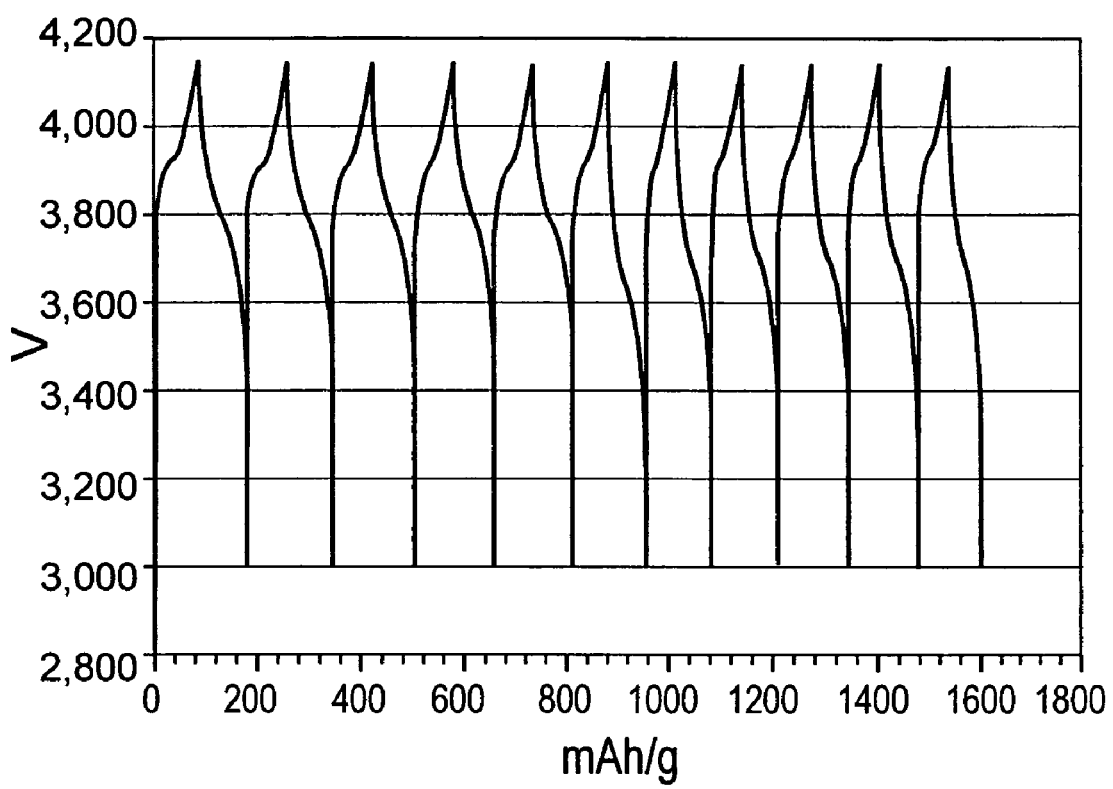

FIGS. 1 to 3 show the results of cycling (voltage: 4.15V) the electrochemical cells obtained as described in Examples 1 to 3 respectively.

PREPARATIVE EXAMPLE 1 (PA1)

Firstly, 800 g of xylene were placed in a reaction vessel and heated to 85° C.

Subsequently, addition of a feed stream I consisting of a mixture of 100 g of lauryl acrylate,
300 g of dihydrodicyclopentadienyl acrylate,
120 g of glycidyl methacrylate,
480 g of ethylhexyl acrylate and
2 g of mercaptoethanol, and addition of a feed stream II consisting of
30 g of Wako V 59 (azo initiator V 59) and
200 g of xylene were commenced simultaneously.

Feed stream I was fed into the initial charge over a period of 1.5 hours and feed stream II was fed in over a period of 2 hours. During the addition, the temperature was held in the range from 80 to 90° C. The reaction mixture was subsequently allowed to react for another 3 hours at 90° C.

A mixture consisting of 166 g of 4-hydroxybenzophenone and 0.83 g of dimethylaminopyridine was then added. The reaction mixture was allowed to react further for from 2 to 3 hours until an epoxide value of <0.01 had been reached.

PREPARATIVE EXAMPLE 2 (PA2)

Firstly, 660 g of xylene were placed in a reaction vessel and heated to 85° C.

Subsequently, a feed stream I consisting of 200 g of dihydrodicyclopentadienyl acrylate 80 g of glycidyl methacrylate and 580 g of ethylhexyl acrylate and a feed stream II consisting of 30 g of Wako V 59 (Azo initiator V 59) and 200 g of xylene were fed simultaneously into the initial charge over a period of 1.5 hours (feed stream I) and over a period of 2 hours (feed stream II). During the addition, the temperature was held in the range from 80 to 90° C.

The reaction mixture was subsequently allowed to react for another 3 hours at 90° C. Subsequently, a mixture consisting of 110.67 g of 4-hydroxybenzophenone and 0.83 g of dimethylaminopyridine, was added. The reaction mixture was then allowed to react further for from 2 to 3 hours until an epoxide value of <0.01 had been reached.

EXAMPLE 1

20 g of a wollastonite hydrophobicized with methacrylsilane (Tremin® 283–600 MST) were dispersed in 15 g of acetone. Subsequently, 54 g of a solution of 6 g of a vinylidene fluoride-hexafluoropropylene copolymer (Kynarflex® 2801, ELF-Atochem) and a solution of 4.6 g of PA1, prepared as described in Preparative Example 1, in 34 g of xylene were added. Finally, 2.8 g of tris-(2-ethylhexyl) phosphate were added.

The composition obtained in this way was subsequently applied at 60° C. to a support material by means of a doctor blade having a slit opening of 500 μm, the solvents were removed over a period of 5 minutes and, after pulling off the dried coating, a film having a thickness of about 30 μm was obtained. This was photocrosslinked by illumination for 10 minutes at a distance of 5 cm under a field of superactinic fluorescent tubes (TL 09, Philips).

The film obtained in this way was used as a solid electrolyte and combined with $LiCoO_2$ as cathode and graphite as anode to produce a round sandwich cell. An electrochemical cell was obtained using $LiPF_6$ as electrolyte salt and a 1:1 mixture of ethylene carbonate and diethylene carbonate as liquid electrolyte and this cell was cycled by application of a voltage of 4.15V.

The specific battery data achieved by means of this cell were as follows:

| Battery test | | | | |
|---|---|---|---|---|
| Cycle No. | Half cycle | Cuff. density [mA/cm$^2$] | Specific capacity [mAh/g] | |
| | | | Charge | Discharge |
| 1 | c (Li out) | 0.5 | 118.8 | |
| | d (Li in) | −1.0 | | 110.2 |
| 2 | c (Li out) | 0.5 | 109.0 | |
| | d (Li in) | −1.0 | | 109.5 |
| 3 | c (Li out) | 0.5 | 107.9 | |
| | d (Li in) | −1.0 | | 108.7 |
| 4 | c (Li out) | 0.5 | 106.7 | |
| | d (Li in) | −1.0 | | 107.5 |
| 5 | c (Li out) | 0.5 | 105.5 | |
| | d (Li in) | −1.0 | | 106.4 |
| 6 | c (Li out) | 0.5 | 103.4 | |
| | c (Li out) | 0.25 | 4.6 | |
| | d (Li in) | −2.0 | | 100.0 |
| 7 | c (Li out) | 1.0 | 85.5 | |
| | d (Li in) | −2.0 | | 91.5 |
| 8 | c (Li out) | 1.0 | 89.6 | |
| | d (Li in) | −2.0 | | 89.9 |
| 9 | c (Li out) | 1.0 | 88.4 | |
| | d (Li in) | −2.0 | | 88.4 |
| 10 | c (Li out) | 1.0 | 87.4 | |
| | d (Li in) | −2.0 | | 87.3 |
| 11 | c (Li out) | 1.0 | 86.8 | |
| | d (Li in) | −2.0 | | 86.8 |

Cathode area: 1 cm$^2$
Anode area: 1 cm$^2$
Weight per unit area of cathode: 263.6 g/m$^2$
Electrolyte: 1M $LiPF_6$/ethylene carbonate (EC): diethylene carbonate (DEC) = 1:1

The results of this cycling are shown in FIG. 1. As can be seen, this cell possessed, for example, a specific charge capacity at the cathode of 106.4 mAh/g in the fifth cycle.

EXAMPLE 2

A film was produced by a method similar to Example 1 using PA1 as crosslinker system, but a film having a thickness of 40 μm was produced in Example 2.

The film obtained in this way was used as solid electrolyte and combined with $LiCoO_2$ as cathode and graphite as anode to produce a round sandwich-like planar pressure cell (600 N/10 cm$^2$ operating pressure). Using $LiPF_6$ as electrolyte salt and a 1:1 mixture of ethylene carbonate and diethylene carbonate as liquid electrolyte, cycling was carried out at a voltage of about 4.15 V.

The results of this cycling are shown in FIG. 2.

In the 5th cycle, a specific charge capacity at the cathode of about 93 mAh/g was obtained for this cell.

EXAMPLE 3

A composition according to the present invention was prepared in the same way as in Example 1, but this time using a solution of 5 g of PA2 in 32 g of xylene. Furthermore, 2.1 g of tris(2-ethylhexyl) phosphate were used.

A film was produced from this composition in the same way as in Example 1 and this was in turn used to produce an electrochemical sandwich cell by the same method as described in Example 1.

This cell was tested in the same way as the cell obtained in Example 1.

The specific battery data achieved by means of this cell were as follows:

Battery test

| Cycle No. | Half cycle | Curr. density [mA/cm$^2$] | Specific capacity [mAh/g] Charge | Specific capacity [mAh/g] Discharge |
|---|---|---|---|---|
| 1 | c (Li out) | 0.5 | 99.7 | |
|   | d (Li in)  | −1.0 |      | 81.2 |
| 2 | c (Li out) | 0.5  | 87.2 | |
|   | d (Li in)  | −1.0 |      | 80.5 |
| 3 | c (Li out) | 0.5  | 81.7 | |
|   | d (Li in)  | −1.0 |      | 76.5 |
| 4 | c (Li out) | 0.5  | 80.7 | |
|   | d (Li in)  | −1.0 |      | 76.1 |
| 5 | c (Li out) | 0.5  | 79.5 | |
|   | d (Li in)  | −1.0 |      | 75.1 |
| 6 | c (Li out) | 0.5  | 76.7 | |
|   | c (Li out) | 0.25 | 4.1  | |
|   | d (Li in)  | −2.0 |      | 70.3 |
| 7 | c (Li out) | 1.0  | 60.6 | |
|   | d (Li in)  | −2.0 |      | 63.6 |
| 8 | c (Li out) | 1.0  | 68.1 | |
|   | d (Li in)  | −2.0 |      | 67.0 |
| 9 | c (Li out) | 1.0  | 68.6 | |
|   | d (Li in)  | −2.0 |      | 67.0 |
| 10 | c (Li out) | 1.0 | 67.8 | |
|    | d (Li in)  | −2.0 |     | 66.2 |
| 11 | c (Li out) | 1.0 | 68.1 | |
|    | d (Li in)  | −2.0 |     | 66.2 |

Cathode area: 1 cm$^2$
Anode area: 1 cm$^2$
Weight per unit area of cathode: 263.6 g/m$^2$
Electrolyte: 1M LiPF$_6$/ethylene carbonate (EC): diethylene carbonate (DEC) = 1:1
Discharge capacity (5th cycle): 75 mAh/g
Discharge capacity (11th cycle): 66 mAh/g
Discharge rate (3.0 mA/cm$^2$): 87%

We claim:

1. A composition comprising
  (a) from 1 to 99% by weight of a solid (I) which is selected from a group consisting of compounds Ia, Ib, Ic, mixtures of compounds Ia and Ib, and mixtures of compounds Ia and Ic, wherein the compounds have a primary particle size of from 5 nm to 100 μm, and which solid (I) is insoluble in a liquid electrolyte suited for use in an electrochemical cell,
  (b) from 1 to 99% by weight of a polymeric material (II), wherein
  the compound Ia is selected from the group consisting of inorganic oxides, mixed oxides, silicates, sulfates, carbonates, phosphates, nitrides, amides, imides and carbides of the elements of main groups I, II, III and IV and transition group IV of the Periodic Table, polymers selected from the group consisting of polyethylene, polypropylene, polystyrene, polytetraflouroethylene, polyvinylidene fluoride, polyamides and polyimides; dispersions comprising said polymers; and a mixture of two or more thereof;
  the compound Ib is selected from the group consisting of LiCoO$_2$, LiNiO$_2$, LiNi$_x$Co$_y$O$_2$ and LiNi$_x$Co$_y$Al$_z$O$_2$, where 0<x,y,z≦1, Li$_x$MnO$_2$ (0<x≦1), Li$_x$Mn$_2$O$_4$ (0<x≦2), Li$_x$MoO$_2$ (0<x≦2), Li$_x$MnO$_3$ (0<x<1), LiMnO$_2$ (0<x≦2), Li$_x$Mn$_2$O$_4$ (0<x≦2), Li$_x$V$_2$O$_4$ (0<x≦2.5), Li$_x$V$_2$O$_3$ (0<x≦3.5), Li$_x$VO$_2$ (0<x≦1), LiWO$_2$ (0<x≦1), Li$_x$WO$_3$ (0<x≦1), Li$_x$TiO$_2$ (0<x≦1), Li$_x$Ti$_2$O$_4$ (0<x≦2), Li$_x$RuO$_2$ (0<x≦1), Li$_x$Fe$_2$O$_3$ (0<x≦2), Li$_x$Fe$_3$O$_4$ (0<x≦2), Li$_x$Cr$_2$O$_3$ (0<x≦3), Li$_x$Cr$_3$O$_4$ (0<x≦3.8), Li$_x$V$_3$S$_5$ (0<x≦1.8), Li$_x$Ta$_2$S$_2$ (0<x≦1), Li$_x$FeS (0<x≦1), Li$_x$FeS$_2$ (0<x≦1), Li$_x$NbS$_2$ (0<x≦2.4), Li$_x$MoS$_2$ (0<x≦3), Li$_x$TiS$_2$ (0<x≦2), Li$_x$ZrS$_2$ (0<x≦2), Li$_x$NbSe$_2$ (0<x≦3), Li$_x$VSe$_2$ (0<x≦1), Li$_x$NiPS$_2$ (0<x≦1.5), Li$_x$FePS$_2$ (0<x≦1.5), LiNi—$^B_{1-x}$O$_2$ (0<x<1), LiNi$_x$Al$_{1-x}$O$_2$ (0<x<1), LiNi$_x$Mg$_{1-x}$O$_2$ (0<x<1), LiNi$_x$Co$_{1-x}$VO$_4$ (1>x>0), LiNi$_x$Co$_y$Mn$_z$O$_2$ (x+y+z=1), LiFeO$_2$, LiCrTiO$_4$, Li$_a$M$_b$L$_c$O$_d$ (1.15>a>0; 1.3>b+c>0.8; 2.5>d>1.7; M=Ni, Co, Mn; L=Ti, Mn, Cu, Zn, alkaline earth metal), LiCu—$^{II}$Cu$_y^{III}$Mn$_{(2>x+y)}$O$_4$ (2>x+y≧0), LiCrTiO$_4$, LiGa$_x$Mn$_{2-x}$O$_4$ (0.1≧x≧0), poly(carbon sulfides), V$_2$O$_5$; and a mixture of two or more thereof,
  the compound Ic is selected from the group consisting of lithium, a lithium-containing metal alloy, micronized carbon black, natural and synthetic graphite, synthetically graphitized carbon powder, a carbon fiber, titanium oxide, zinc oxide, tin oxide, molybdenum oxide, tungsten oxide, titanium carbonate, molybdenum carbonate, zinc carbonate, Li$_x$M$_y$SiO$_z$ (1>x≧0.1>y≧0, z>0), Sn$_2$BPO$_4$, conjugated polymers, lithium metal compounds; and a mixture of two or more thereof,
  and wherein
  where the solid (I) is the mixture of Ia and Ib, the composition further comprises from 0.1 to 20% by weight, based on the total weight of components I and II, of conductive carbon black; and where the solid (I) is the mixture of Ia and Ic, the composition further comprises up to 20% by weight, based on the total weight of the components I and II, of conductive carbon black;
  and wherein said polymeric material (II) comprises
    from 1 to 100% by weight of a polymer or copolymer (IIa) which has, as part of the polymer chain, at the end(s) of said chain and/or laterally on said chain, reactive groups (RG) which are capable of crosslinking reactions under the action of heat and/or UV radiation, and from 0 to 99% by weight of at least one polymer or copolymer (IIb) which is free of reactive groups (RG);
  and wherein the polymer (IIa) has, as reactive groups (RG),
    at least one reactive group RGa which in the triplet excited state under the action of heat and/or UV radiation is capable of hydrogen abstraction, and
    at least one group RGb which is different from RGa and is coreactive with RGa,
  with at least one group RGa and at least one group RGb being present on average over all polymer molecules,
  wherein the polymer (IIa) is a polymer or copolymer of an acrylate or methacrylate and has reactive groups RGa which comprise benzophenone units and reactive groups RGb which comprise dihydrodicyclopentadiene units.

2. The composition as claimed in claim 1, wherein the polymer (IIb) is selected from the group consisting of
  a polymer or copolymer of vinyl chloride, acrylonitrile, vinylidene fluoride;
  a copolymer of vinyl chloride and vinylidene chloride, vinyl chloride and acrylonitrile, vinylidene fluoride and hexafluoropropylene, vinylidene fluoride and hexafluoropropylene;
  a terpolymer of vinylidene fluoride and hexafluoropropylene together with a member of the group consisting of vinyl fluoride, tetrafluoroethylene and trifluoroethylene.

3. The composition as claimed in claim 1, wherein the polymer (IIb) is a copolymer of vinylidene fluoride and hexafluoropropylene.

4. A composite comprising at least one first layer and at least one second layer, wherein the first and the second layer are obtained by crosslinking a composition as defined in claim 1, and wherein the first layer comprises the compound Ib or the compound Ic, and the second layer comprises the compound Ia and is free of the compounds Ic and Ib.

5. A method of producing the composite defined in claim 4 which comprises (I) producing the at least one first layer by crosslinking the composition comprising the compound Ib or the compound Ic thermally or by irradiation with ionic or ionizing radiation, an electron beam, UV or visible light, by electrochemically induced polymerization or by ionic polymerization, (II) producing the at least one second layer by crosslinking the composition comprising the compound Ia and being free of the compounds Ib and Ic thermally or by irradiation with ionic or ionizing radiation, an electron beam, UV or visible light, by electrochemically induced polymerization or by ionic polymerization, and (III) combining the at least one first layer and the at least one second layer by means of a conventional coating process.

6. A solid selected from the group consisting of an electrolyte, a separator, an electrode, a sensor, an electrochromic window, a display, a capacitor and an ion-conducting film, which solid comprises the composite defined in claim 4.

7. An electrochemical cell comprising the solid electrolyte, the separator or the electrode defined in claim 6.

8. A method of producing a crosslinked composition which comprises providing the composition defined in claim 1 and crosslinking the composition thermally, or by irradiation with ionic or ionizing radiation, an electron beam, UV or visible light, by electrochemically induced polymerization, or by ionic polymerization.

9. A solid selected from the group consisting of an electrolyte, a separator, an electrode, a sensor, an electrochromic window, a display, a capacitor and an ion-conducting film, which solid comprises the crosslinked composition obtained by the method of claim 8.

10. An electrochemical cell comprising the solid electrolyte, the separator or the electrode defined in claim 9.

* * * * *